(12) United States Patent
Hüttmann et al.

(10) Patent No.: US 8,399,839 B2
(45) Date of Patent: Mar. 19, 2013

(54) INFRARED OPTICAL GAS-MEASURING DEVICE

(75) Inventors: Horst Hüttmann, Uetersen (DE); Andreas Moldt, Lübeck (DE)

(73) Assignee: Dräger Safety AG & Co. KGaA, Lübeck (DE)

(*) Notice: Subject to any disclaimer, the term of this patent is extended or adjusted under 35 U.S.C. 154(b) by 438 days.

(21) Appl. No.: 12/773,194

(22) Filed: May 4, 2010

(65) Prior Publication Data
US 2011/0031402 A1 Feb. 10, 2011

(30) Foreign Application Priority Data

Aug. 5, 2009 (DE) .................. 10 2009 036 114

(51) Int. Cl.
*G01N 21/17* (2006.01)
(52) U.S. Cl. ......................................... 250/343
(58) Field of Classification Search .......... 250/343, 250/351
See application file for complete search history.

(56) References Cited

U.S. PATENT DOCUMENTS

| | | | | |
|---|---|---|---|---|
| 3,175,092 A | * | 3/1965 | Leftwich | 250/233 |
| 4,101,221 A | * | 7/1978 | Schunck et al. | 356/434 |
| 5,475,222 A | | 12/1995 | King | |
| 6,989,549 B2 | * | 1/2006 | Diekmann et al. | 250/573 |
| 7,541,587 B2 | * | 6/2009 | Cutler et al. | 250/339.13 |
| 2004/0007667 A1 | | 1/2004 | Diekmann et al. | |
| 2008/0308733 A1 | | 12/2008 | Doncaster | |

FOREIGN PATENT DOCUMENTS

| | | |
|---|---|---|
| DE | 102 00 908 A1 | 7/2003 |
| JP | 2009 145125 A | 7/2009 |
| WO | WO 2005/054827 | 6/2005 |
| WO | WO 2007/091043 | 8/2007 |

* cited by examiner

*Primary Examiner* — Constantine Hannaher
(74) *Attorney, Agent, or Firm* — McGlew and Tuttle, P.C.

(57) ABSTRACT

A first, upper slotted disk (10) and a second, lower slotted disk (20) are arranged as a gas inlet (11) in a gas-measuring device (1). The first, upper slotted disk (10) and the second, lower slotted disk (20) are connected to one another and to a sensor housing (2) via a spacer element (29). The arrangement of the slotted disks (10, 20) in relation to one another is selected to be such that reduced propagation of light of an infrared radiation source (43) through both slotted disks (10, 20) into the measuring environment is achieved.

20 Claims, 15 Drawing Sheets

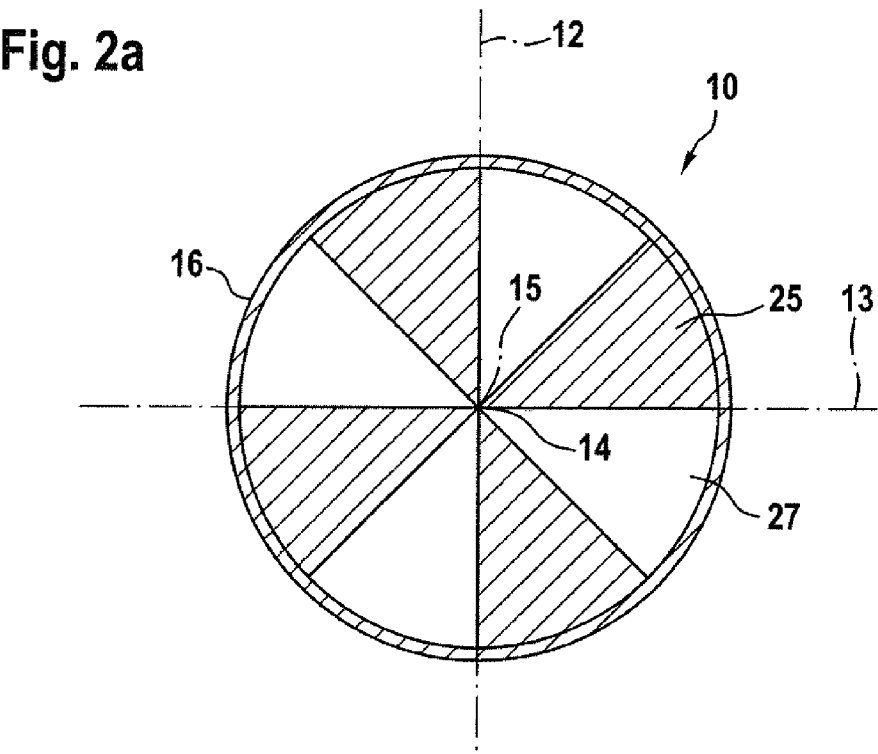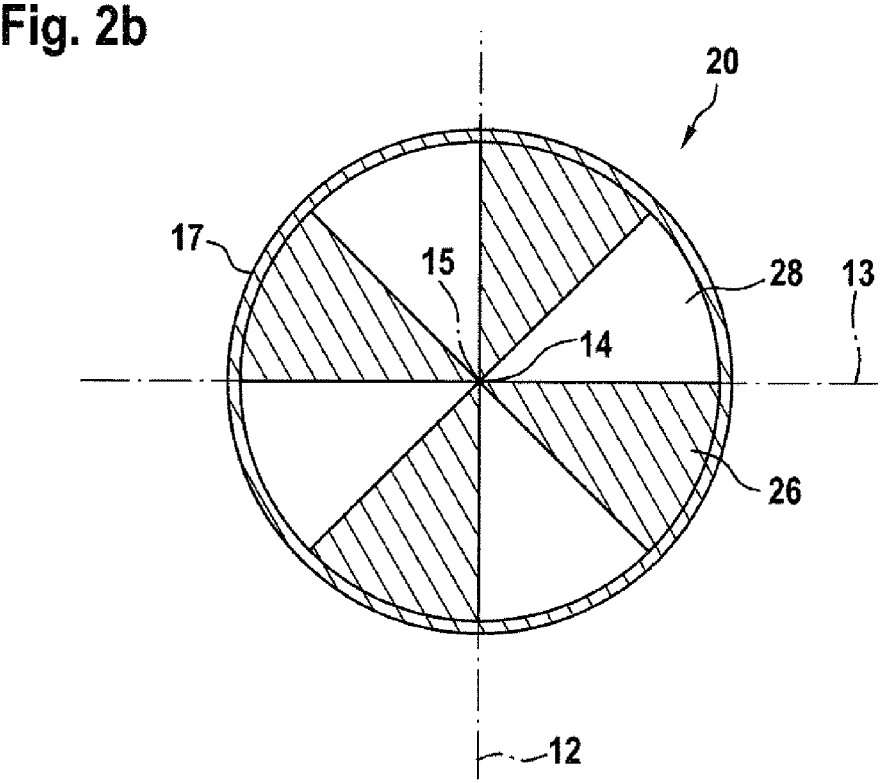

INFRARED OPTICAL GAS-MEASURING DEVICE

CROSS REFERENCE TO RELATED APPLICATIONS

This application claims the benefit of priority under 35 U.S.C. §119 of German Patent Application DE 10 2009 036 114.6 filed Aug. 5, 2009, the entire contents of which are incorporated herein by reference.

FIELD OF THE INVENTION

The present invention pertains to an infrared optical gas-measuring device.

BACKGROUND OF THE INVENTION

Gas sensors based on the infrared optical measurement principle are known from the state of the art and are used to monitor gas concentrations in industry for many different applications. The gas sensors detect increased concentrations of explosive gases or gases harmful to the human body, for example, methane (CH4) and carbon dioxide (CO2) and are integrated in warning and alarm systems.

An infrared optical gas sensor, in which the gas enters the sensor housing via a perforated plate, is known from WO 2005/054827. The perforated plate represents an upper limitation of a gas-filled part of the sensor housing, into which the gas to be measured enters via the perforations formed in the perforated plate. A radiation source and an optical detector are arranged in the interior of the gas sensor in a bottom part, which represents the lower limitation of the gas-filled part of the sensor housing.

The IR radiation is sent by the radiation source and is reflected at the perforated plate towards the optical detector. The intensity reaching the detector is an indicator of the measured gas concentration based on the optical absorption caused by the gas. The gas species is selected and the attainable measuring sensitivity and measuring accuracy are determined by the selected wavelength range of the infrared radiation combined with the dimensions of the gas-filled part of the sensor housing, the so-called measuring gas cell.

The gas entry shown in WO 2005/054827 via a perforated plate allows the measuring gas to enter the measuring gas cell via the total area of the perforations in the perforated plate, on the one hand, and, on the other hand, part of the emitted light is lost through the perforations in the perforated plate in the measuring environment, so that this part of the light cannot be reflected onto the detector. The selection of the dimension, position and quantity of perforations in the perforated plate defines, on the one hand, the loss of light to the measuring environment but, on the other hand, also the velocity of entry of the measuring gas into the measuring gas cell.

WO 2007/091043 A1 discloses a gas sensor, whose measuring gas cell is spherical for guiding the propagation of the optical rays, wherein the guiding of the optical radiation brings about focusing of the rays to the detector and thus increases the intensity of the light falling on the detector.

The extent of loss of light, both through the gas inlet opening and due to the absorption in the gas, determines the intensity of the radiation at the detector. The velocity at which the measuring gas enters the measuring gas cell determines the rise time of the gas sensor, which is often called the t10-90 time and provides information on the time at which a measured value rises from a level of 10% of the final value to a level corresponding to 90% of the final value.

SUMMARY OF THE INVENTION

Based on the state of the art, the object of the present invention is to provide a gas-measuring device of the said type, in which the loss of light is reduced.

Furthermore, an object of the present invention is to use slotted disks or perforated disks in the area of a gas inlet opening of a gas-measuring device of the type mentioned.

The gas-measuring device according to the present invention comprises a gas inlet opening for an infrared optical gas sensor, comprising two disks, which are arranged at spaced locations from one another and are provided with perforations and/or slots as gas passage openings, which close a preferably pot-shaped sensor housing with integrated bottom section on the top side, forming a measuring gas cell.

At least one light passage for passing through infrared light from at least one radiation source into the measuring gas cell and for passing through the light from the measuring gas cell onto at least one light-sensitive detector is provided in the bottom section. The light passages make it possible to radiate the infrared light from the at least one radiation source arranged under the bottom section or integrated in the bottom section into the measuring gas cell filled with the measuring gas and to optically couple the reflected rays with the at least one light-sensitive detector arranged under or above the bottom section. The bottom section accommodates the light passages. The light passages are preferably planar and flat. The light passages are made, in another preferred manner, essentially parallel to the two disks, which are designed as gas passage openings and are provided with perforations or slots.

The reception spectra of the at least one light-sensitive detector are preferably adapted to the radiation spectra of the at least one radiation source and the absorption range of the gas to be measured.

The optical wavelength range of the at least one radiation source is preferably selected here correspondingly depending on the measuring gas to be detected. Gaseous hydrocarbons and other gaseous hydrocarbon compounds are preferably measured. For example, the absorptions of propane ($C_3H_8$) and methane ($CH_4$) are in the wavelength range of 3.3 μm to 3.5 μm. The absorption of carbon dioxide ($CO_2$) is in the wavelength range of 4.2 μm to 4.3 μm and the absorption of carbon monoxide (CO) is in the wavelength range of 4.5 μm to 4.85 μm.

The light passages are preferably designed as disks made of a material transparent to light for the preferred wavelength range, preferably glass, and in another preferred manner of sapphire crystal with a crystal thickness in the range of 0.2 mm to 1.0 mm. The spectral transmission band of the sapphire disks is in the range of 3 μm to 5 μm. In a preferred embodiment, the bottom section accommodates a light passage for the infrared radiation source arranged under the bottom section and a light passage each for at least one optical detector, which is arranged under the bottom section and which is designed to detect infrared light.

In another preferred variant of this preferred embodiment, at least two optical detectors are connected to the measuring gas cell via at least two light passages in a light-conducting manner.

In another preferred manner, the at least one light passage for feeding the light into the measuring gas cell of the at least one radiation source is designed as a first sapphire disk, which is arranged on the top side of the bottom section in the measuring gas cell. The first sapphire disk is connected to the bottom section in a gas-tight manner, so that no gas can enter from the measuring gas cell into the first functional area of the gas sensor, which said area is located under the bottom section. This first functional area is thus free from measuring gas and contains the radiation source as well as corresponding electronic components for operating and actuating the radiation source.

The first sapphire disk is preferably arranged on the top side on the bottom section by means of a gas-tight bonded connection or by sealing.

The gas-tight separation of the first functional area from the measuring gas cell has the advantage that no measuring gas can enter the first functional area and ignition of a quantity of measuring gas in the first functional area is not therefore possible. Such a gas-measuring device is thus suitable, in principle, for use in potentially explosive areas.

In another preferred manner, the light passage for decoupling the light from the measuring gas cell to the at least one detector is designed as an at least one second sapphire disk, which is arranged on the underside of the bottom section in the measuring gas cell. The second sapphire disk separates the measuring gas cell from a second functional area located under the bottom section. This second functional area contains the at least one detector, which is designed to detect infrared light, as well as corresponding electronic components for operating and receiving the measuring signals of the at least one detector.

The at least second sapphire disk is preferably connected to the bottom section in a gas-tight manner by means of a bonded connection, and in another preferred manner it is bonded on the underside to the bottom section, so that no gas can enter from the measuring gas cell into the second functional area of the gas sensor and the second functional area is thus free from measuring gas. The gas-tight separation of the second functional area from the measuring gas cell has the advantage that no measuring gas can enter the second functional area and ignition of a quantity of measuring gas in the second functional area is thus not possible.

In another preferred manner, the first and second functional areas are separated from one another in a gas-tight manner and/or are insulated electrically from one another, so that it is possible to locally limit an error if there is a cause of error in one of the two functional areas. The separation of the first functional area from the second functional area is preferably brought about by means of a wall arranged between the first and second functional areas. Such a gas-measuring device is thus suitable for use in potentially explosive areas.

The bottom section is preferably designed to reflect light in the infrared optical range, with the exception of areas on the surface needed in space by the light passages. Bottom section surface designs suitable for reflection act as reflectors here and may consist, for example, of metallically reflective coatings of the surface of the bottom section, preferably coatings consisting of gold. A gold coating of the surface of the bottom section in a thickness in the range of 0.05 µm to 5 µm is a typical value here. The bottom section itself preferably consists essentially of a dimensionally stable material, more preferably plastic, and it can be prepared in a preferred manner by a plastic injection molding process.

In a preferred embodiment, the surface of the bottom section is made at least partly planar and flat due to accommodating the light passages. Another part of the surface of the bottom section is not made planar or flat but is partly provided with at least one elevation protruding into the measuring gas cell. This elevation is designed, for example, in the form of pyramid-like, truncated pyramid-like, cone-like or truncated cone-like elements.

In yet another preferred embodiment, the surfaces of the side walls of the preferably pot-shaped sensor housing are made reflective on the inside. Surface designs of the preferably pot-shaped sensor housing, which are suitable for reflection, may consist, for example, of metal or reflective coatings of the surface of the preferably pot-shaped sensor housing, preferably of gold.

An inside coating of the surfaces of the side walls of the sensor housing with gold in a thickness of about 0.3 µm is a typical value in the technical application.

The preferably pot-shaped sensor housing preferably consists here essentially of plastic and can be manufactured, in another preferred manner, by a plastic injection molding process.

In one embodiment according to the present invention, the gas feed from the measuring environment into the measuring gas cell of the measuring means is designed by an arrangement of a first, upper slotted or perforated disk and a second, lower slotted or perforated disk arranged at a vertically spaced location from, under and essentially in parallel to the first slotted or perforated disk, which said arrangement is designed as a gas feed opening, wherein slots transparent to light and permeable to gas in the first and second slotted or perforated disk are arranged offset from one another. An essentially parallel arrangement of slotted disks or perforated disks is designed in the sense of the present invention as arrangements in which the slotted disks or perforated disks are either arranged completely in parallel to one another or the arrangement has a maximum angle in the range of 0.5° to 2° for each disk in relation to the horizontal or with a maximum angle in the range of 1° to 3° for the disks in relation to one another.

The undersides of the slotted or perforated disks facing the measuring gas cell are designed so as to reflect light in the infrared optical range. Designs of the slotted or perforated disks that are suitable for reflection may consist, for example, by slotted or perforated disks of metal, preferably polished metal, preferably gold. In an alternative embodiment, the slotted or perforated disks may consist of disks made of dimensionally stable materials, such as plastic or metal disks, which are coated with metal, preferably gold. An underside coating with gold in a thickness of about 0.2 µm shall be mentioned as an example here.

The material thickness of the slotted or perforated disks is in a range of 0.1 mm to 1.5 mm, and the first, upper slotted or perforated disk is preferably made with a greater material thickness than the second, lower slotted or perforated disk, because the first, upper slotted or perforated disk may additionally also assume the function of offering mechanical protection against the environment besides the function of feeding gas. An exemplary value for the material thickness of a first, upper slotted or perforated disk provided with an additional mechanical protection is a value of 0.4 mm. An exemplary value for the material thickness of a first, upper slotted or perforated disk without additional mechanical protection is a value of 0.2 mm, and an exemplary value for the material thickness of the second, lower slotted or perforated disk is a value of 0.2 mm.

The slots or perforations are prepared in the slotted or perforated disk, for example, by a chemical etching process or by a laser cutting process.

The flow of gas from the measuring environment into the sensor takes place in the direction of the measuring gas cell at first essentially at right angles through the slots or perforations of the first slotted or light passage into the space formed by the spacing between the first and second slotted or perforated disks. The gas then flows essentially horizontally through the gap formed by the spacing between the first and second slotted or perforated disks and finally essentially again at right angles through the slots or perforations of the second slotted or perforated disk and into the measuring gas cell. The measuring gas enters the measuring gas cell in this manner.

The light is emitted from the radiation source in the bottom section essentially linearly in the direction of the gas inlet opening arranged on the top side of the pot-shaped sensor housing, a first part is reflected on the first, upper slotted or perforated disk, and a second part is reflected on the second, lower slotted or perforated disk. The light is reflected in this manner nearly completely after passing through the measuring gas cell through the arrangement of the first and second slotted or perforated disk.

A first quantity of the infrared optical light of the at least one radiation source passes in this manner through the measuring gas cell filled with the measuring gas at least twice and reaches the at least first detector.

A second quantity of the light is reflected on the reflective surfaces of the bottom section and passes again through the measuring gas cell, is reflected partly on the second, lower slotted or perforated disk, partly on the first, upper slotted or perforated disk, partly at the edges of the first or second slotted or perforated disk and propagates after reflection in the direction of the bottom section and/or the side walls of the sensor housing.

A portion of the light that was reflected in a direction of the light passages arranged in the bottom section with optical detectors under it enters the range of detection of the at least first optical detector.

Light that was reflected in the direction of the light passage arranged in the bottom section with the radiation source located under it does not enter the range of detection of the optical detectors, is not essentially reflected on the light passages and cannot therefore enter the range of detection of the at least first optical detector any more and thus it cannot contribute to the measured signal any more.

Another portion of the light, which was reflected in the direction of the light passages arranged in the bottom section, is reflected on the reflective surfaces of the bottom section and is sent partly in the direction of the first and second slotted or perforated disk, where it is partly reflected again.

Thus, portions of the light pass through the measuring gas cell twice, and other portions of the light pass through the measuring gas cell four or more times before they make a contribution to the measured signal at the at least first optical detector.

In an especially preferred variant of this embodiment according to the present invention, the slotted disks are formed by an arrangement of a sequence of slotted circle segments that are transparent to light and permeable to gas alternating with full circle segments. The two slotted disks, which are located at spaced locations from one another essentially in parallel to one another, are made with a number of circle segments, comprising a sequence of slotted circle segments and full circle segments. The number of circle segments of the first, upper slotted disk and second, lower slotted disk is preferably identical. A number of segments equaling 8 to 16 segments and preferably a number of segments equaling 8 segments has proved to be advantageous for a simple and robust construction.

The measuring technical properties in the technical design application can be set by selecting the number of segments and the particular size of the openings of the segments of the first, upper slotted disk and second, lower slotted disk and by selecting the distance between the first, upper slotted disk and second, lower slotted disk, resulting in a ratio between light reflection and signal rise time.

The slotted circle segments are formed from a slotted disk made of a solid material as free surfaces in the slotted disk, which are transparent to light and permeable to gas, and the full circle segments and a remaining edge consisting of solid material on the circumference of the slotted disk form the rest of the nonslotted segments of the slotted disk.

The slotted disks, which are located at spaced locations from one another, are offset by one circle segment each in relation to one another, so that the slotted circle segments of the upper slotted disk are arranged in the vertical direction above full circle segments of the lower slotted disk and the full circle segments of the upper slotted disk are arranged in the horizontal direction above the slotted circle segments of the lower slotted disk. This offset makes possible a nearly complete reflection of the infrared optical light emitted by the first radiation source at the arrangement of the first and second slotted disks for a light falling on the arrangement of the first and second slotted disks essentially from a vertical angle. The range of an essentially right angle comprises in the sense of the present invention a light incidence in the vertical direction from the radiation source upwards starting through the light passage into the measuring gas cell onto the arrangement of the first and second slotted disks in an angle range of 85° to 90°.

The extension of the full circle segments in terms of area is preferably selected to be greater than that of the slotted circle segments, so that there is an overlap in terms of area in the horizontal direction of the first and second slotted disks. This overlap in terms of area advantageously prevents light from being able to pass in the vertical direction through the vertical arrangement of the two slotted disks and makes possible a nearly complete reflection of the infrared optical light emitted by the first radiation source at the arrangement of the first and second slotted disks even for portions of light that fall on the arrangement of the first and second slotted disks from an essentially non-vertical angle. These portions of light arise from the complex optical conditions in the measuring gas cell, due to the construction and reflective surface design of the insides of the preferably pot-shaped sensor housing, the bottom section and the first, upper slotted disk and second, lower slotted disk. A large number of variables, for example, the nature and angle of inclination of the surfaces, as well as light diffraction and light refraction effects, play a role here. For example, such special light components are obtained from a simplified view of the complex optical conditions if parts of the light are reflected or refracted at an edge of a circle segment in a manner not defined more specifically, propagate, furthermore, in the measuring gas cell in a manner not defined more specifically and in an unforeseeable manner, are subsequently reflected, possibly multiple times, for example, at the bottom section or at the side walls of the measuring gas cell and fall as a result on the arrangement of the first and second slotted disks at an essentially no longer vertical angle. The range of essentially non-right angles comprises in the sense of the present invention a light incidence in the vertical direction from the radiation source in the upward direction starting through the light passage into the measuring gas cell onto the arrangement of the first and second slotted disks in the angle range of 70° to 85°. In case of identical number of slotted circle segments and full circle segments of the first, upper slotted disk and second, lower slotted disk, an overlap in terms of area can be achieved by the opening angle of the slotted circle segment being made smaller than the opening angle of the full circle segment. The overlap in terms of area may also be achieved by a symmetrical reduction of the area of the slotted circle segment by shortening and displacing the side lengths of the circle cutout of the slotted circle segment compared to the full circle segment. Combinations of angle reduction and symmetrical reduction by shortening the three side lengths of the circle cutouts of the slotted circle segments to avoid the vertical passage of light through the arrangement of the two slotted disks are also covered as design features in the sense of the present invention.

The slotted disks have an essentially round, oval or circular shape in a special embodiment, and the slots in the slotted disks are designed essentially as circle segments rotationally symmetrically to the center.

In another design of the embodiment according to the present invention, the slotted disks have an essentially round, oval or circular shape and the slots in the slotted disks are designed essentially as slots or circle segments rotationally symmetrically to a reference point of the essentially round, oval or circular slotted disks, which said reference point is different from the center.

A point that is located between the center of the slotted disk and a point along the circumference of the slotted disk is selected here as the reference point for the rotationally symmetrical arrangement of the slots or circle segments. Circle segments of unequal areas are obtained in this other preferred embodiment of the first embodiment due to the shifting of the symmetry of rotation from the center of the slotted disk to the reference point located outside the center, and the circle segments that are located on the side of the center located opposite the reference point have a greater extension in terms of area than the circle segments located on the side that is located on the side of the reference point. This unequal arrangement of the circle segments in the slotted disk is advantageously adapted to the arrangement in space of the radiation source and of the at least one optical detector in the bottom section as well as to the light passages for the radiation source and for the at least one optical detector. The circle segments having a larger area have a larger opening area for the entry of gas and are arranged above the optical detectors. It is thus achieved that gas preferably enters towards zones of the highest light intensity of the optical ray path in the measuring gas cell, so that, on the one hand, the quantity of gas that locally exists (is present) in this essential and dominant optical ray path from the radiation source to the optical detector can enter the measuring gas cell through the one, largest possible gas inlet opening and the rate of gas exchange is locally relatively increased in that part of the measuring gas cell. On the other hand, the arrangement of unequal circle segments leads to a locally enlarged reflection surface, which leads, as it were, to a guiding of the light within the measuring gas cell along optical paths that are favorable due to the arrangement in space of the radiation source and of the detectors.

The optical path can thus be adapted to both the arrangement in space of the radiation source and of the detectors and the wavelength ranges of the measuring gases to be detected with the gas-measuring device, equaling 3.3 µm to 3.5 µm or 4.2 µm to 4.3 µm or 4.5 µm to 4.85 µm.

The adapted coordination of the optical paths and of the optical path lengths with the wavelengths of the measuring gases leads to improved selectivity of measurement, to an improved signal at the optical detectors, hence to an improved signal-to-noise ratio and to better measuring resolution compared to a nonadapted coordination.

In case of a asymmetrical arrangement of the light passages with the radiation source and the infrared detectors, an asymmetrical arrangement of the circle segments in the slotted disks, which arrangement is adapted thereto, leads to an improved signal response time and signal intensity compared to a symmetrical arrangement of the circle segments in the slotted disks. The measuring technical properties can be set in the technical design application by selecting the asymmetry of the arrangement of the segments in the slotted disks as well as by selecting the number of segments and the particular size of the openings of the segments of the first, upper slotted disk and second, lower slotted disk and by selecting the distance between the first, upper slotted disk and second, lower slotted disk, resulting in a ratio between light reflection and signal rise time.

In another variant of the embodiment according to the present invention, the slotted disks are designed with gas inlet openings comprising an array of star-shaped and/or radiate rectangular or star-shaped and/or radiate oval slots. The slots may be arranged radially symmetrically to the center of the slotted disks or to a reference point located outside the slotted disks. A number of slots equaling 4 to 20 slots and preferably a number of slots equaling 5 slots has proved to be advantageous for a simple and robust construction.

The measuring technical properties in the technical design application can be set by selecting the number and the particular size of the star-shaped and/or radiate rectangular or star-shaped and/or radiate oval slots of the first, upper slotted disk and second, lower slotted disk and by selecting the distance between the first, upper slotted disk and second, lower slotted disk, resulting in a ratio between light reflection and signal rise time.

In another variant of the embodiment according to the present invention, the slotted disks are provided with gas inlet openings comprising an array of a plurality of parallel ring-shaped slotted ring segments originating concentrically from the center or from the eccentric reference point of the slotted disk alternating with ring-shaped ring segments consisting of solid material. The first, upper slotted disk and the second, lower slotted disk are arranged one above the other and at spaced locations from one another such that the slotted ring segments of the first, upper slotted disk and the slotted ring segments of the second, lower slotted disk are arranged in parallel to one another, but also such that the slotted ring segments of the first, upper slotted disk and the slotted ring segments of the second, lower slotted disk are shifted radially in relation to one another and concentrically from the center of the slotted disk such that slotted rings of one slotted disk and ring segments of the other slotted disk are correspondingly arranged one above the other, so that the light emitted by the radiation source is reflected nearly completely back into the measuring gas cell by the arrangement of the first and second slotted disks and almost no portion of the light emitted by the radiation source enters the measuring environment. The ring segments are connected to one another via a number of, for example, 3 to 6 narrow webs to form a slotted disk. A number of ring-shaped slots, equaling 4 to 10 and preferably a number of 6 ring-shaped slots has proved to be advantageous for a simple and robust construction. The measuring technical properties in the technical design application can be set by selecting the number and the size of the ring segments of the first, upper slotted disk and second, lower slotted disk and the distance between the first, upper slotted disk and second, lower slotted disk, resulting in a ratio between light reflection and signal rise time.

In another variant of the embodiment according to the present invention, the slots formed around the reference point as circle segments or star-shaped, radiate, rectangular or oval slots, are not extended fully up to the reference point. Instead, an essentially round opening is present in one of the two slotted disks centrically around this reference point, and the other slotted disk is made nontransparent to light in the corresponding position. Both the first, upper slotted disk may be provided with the essentially round opening or also the second, lower slotted disk may be provided with the essentially round opening in this arrangement.

The slotted disks are provided with gas inlet openings comprising an array of a number of parallel, rectangular or oval slots in another variant of the embodiment according to the present invention. The first, upper slotted disk and the second, lower slotted disk are arranged one above the other and at spaced locations from one another such that the slots of the first, upper slotted disk and the slots of the second, lower slotted disk are arranged in parallel to one another, with the peculiarity that the slots of the first, upper slotted disk and the slots of the second, lower slotted disk are shifted laterally in relation to one another such that slots of one slotted disk are arranged correspondingly one above the other with area parts of the other slotted disk that are not provided with slots, so that the light emitted by the radiation source is reflected back nearly completely from the array of the first and second slotted disks into the measuring gas cell and almost no part of the light emitted by the radiation source will reach the measuring environment. A number of slots equaling 6 to 20 parallel slots is a practical order of magnitude for a technical application. A number of parallel slots equaling 8 with a slot width of about 1 mm is preferably obtained for a slotted disk with a diameter of 18 mm in case of a distance in the range of 0.1 mm to 0.8 mm between the slotted disks.

The measuring technical properties in the technical design application can be set by selecting the number and particular size of the parallel rectangular or parallel oval slots of the first, upper slotted disk and of the second, lower slotted disk and by selecting the distance between the first, upper slotted disk and the second, lower slotted disk, resulting in a ratio between light reflection and signal rise time.

Instead of the number of rectangular or oval slots arranged in parallel, a number of parallel rows of perforations are arranged in a special embodiment of this other variant of the embodiment according to the present invention with a number of preferably circular perforations arranged in a line in an upper disk and a lower disk to form a gas inlet opening, so that a first, upper perforated disk and a second, lower perforated disk are obtained instead of the first, upper slotted disk and the second, lower slotted disk.

The number of perforations in the parallel rows of perforations is made larger here in the rows of perforations in the area of the center of the perforated disks than in the rows of perforations in the area of the circumference of the perforated disk. The first and second perforated disks are arranged at spaced locations one above the other such that the rows of perforations of the first, upper perforated disk and the rows of perforations of the second, lower perforated disk are arranged in parallel to one another with an offset, but also such that the rows of perforations of the first, upper perforated disk and the rows of perforations of the second, lower slotted disk are shifted laterally in relation to one another such that perforations and/or rows of perforations of one perforated disk are always arranged correspondingly one above the other with the area parts of the other perforated disk without perforations and/or rows of perforations, so that the light emitted by the radiation source is reflected nearly completely back by the arrangement of the first and second perforated disks into the measuring gas cell and almost no part of the light emitted by the radiation source reaches the measuring environment.

An expanded possibility and embodiment variant of the offset of the first, upper perforated disk in relation to the second, lower perforated disk or of the perforations of the first, upper perforated disk in relation to the perforations of the second, lower perforated disk arises from the fact that the perforations of the first, upper perforated disk are arranged one above the other corresponding to the spacing between the perforations of the second one, so that the light emitted by the radiation source is reflected nearly completely back into the measuring gas cell by the array of the first and second perforated disks and almost no portion of the light emitted by the radiation source reaches the measuring environment.

A combination of the arrangement of the rows of perforations of the two perforated disks offset in parallel in relation to one another with the corresponding offset of the perforations and the spacing between the perforations of the first, upper perforated disk in relation to the second, lower perforated disk or of the perforations of the first, upper perforated disk in relation to the perforations of the second, lower perforated disk is also an embodiment that can be applied technically.

A number of rows of perforations equaling 6 to 14 rows of perforations and preferably a number of rows of perforations equaling 12 parallel rows of perforations with an array of a plurality of perforations with a diameter of 0.3 mm to 1.2 mm and with a spacing of 0.3 mm to 1.2 mm between perforations corresponding to the diameter has proved to be advantageous for a simple and robust construction.

The measuring technical properties in the technical design application can be set by selecting the number of perforations and rows of perforations and the particular size of the perforations in the first, upper perforated disk and the second, lower perforated disk, resulting in a ratio between light reflection and signal rise time.

The perforations are preferably round, but they may also have another geometric shape, for example, oval, triangular or rectangular.

The present invention also covers a shape of the perforations in which the perforations are not arranged in a line on a row of perforations but are arranged distributed in the area of the first, upper perforated disk and the second, lower perforated disk such that the first, upper perforated disk and the second, lower perforated disk are arranged corresponding to each other in their spaced orientation, such that perforations of one disk are located vertically one on top of another with non-transparent material of the other disk and the light emitted by the radiation source is thus reflected nearly completely back from the arrangement of the first and second perforated disks into the measuring gas cell and almost no portion of the light emitted by the radiation source reaches the measuring environment.

In another variant of the embodiment according to the present invention, the full circle segments and solid material sections and slotted circle segments, slot-like semicircle segments, radiate rectangular or parallel rectangular openings, slots or perforations within one slotted disk or perforated disk are made such that they have unequal areas. The unequal size of the openings leads to reflective areas of different sizes of the first and second slotted disk or perforated disk in this variant of the embodiment according to the present invention.

A reflective surface of a larger area of the first, upper slotted disk or perforated disk compared to the second, lower slotted disk or perforated disk is implemented such that, first, the openings of the first, upper slotted disk or perforated disk, through which the gas flows in the direction of the measuring gas cell through the first, upper slotted disk or perforated disk, are designed to have a smaller overall area than the openings of the second, lower slotted disk or perforated disk and second, the openings of the second, lower slotted disk or perforated disk, through which the gas flows in the direction of the measuring gas cell through the second, lower slotted disk or perforated disk, are designed to have a larger area than the openings of the first, upper slotted disk or perforated disk.

A reflecting surface of a larger area of the second, lower slotted disk or perforated disk compared to the first, upper slotted disk or perforated disk is implemented such that first, the overall area of the openings of the first, upper slotted or perforated disk, through which the gas flows through the first, upper slotted disk or perforated disk in the direction of the measuring gas cell, is designed to be larger than the openings of the second, lower slotted disk or perforated disk, and second, the area of the openings of the second, lower slotted disk or perforated disk, through which the gas flows through the second, lower slotted disk or perforated disk in the direction of the measuring gas cell, is designed to be smaller than the openings of the first, upper slotted or perforated disk, which openings close the measuring gas cell towards the measuring environment on the underside and are made reflective on the underside.

Due to the first, upper and second, lower slotted disk or perforated disk having different areas, it is possible, as it were, to guide the light in the measuring gas cell along optical paths having different designs and different path lengths, because the light is reflected in one case essentially by the second, lower slotted disk or perforated disk and in the other case essentially by the first, upper slotted disk or perforated disk.

Thus, a reflective surface of the upper, first slotted disk or perforated disk compared to the second, lower slotted disk or perforated disk increases the optical path length in the measuring gas cell without the height of the measuring gas cell and hence the measuring gas volume having to be increased and without the effect of different inlet opening s of the two disks, which result therefrom, having to be taken into account for the design of the measuring means. If the measuring gas volume is kept, in principle, as small as possible, the measuring gas cell can be filled with gas very rapidly from the measuring environment in case of corresponding dimensioning of the inlet opening, which becomes noticeable in a low rise time in case of a change in the gas concentration in the measuring environment.

This design of the light reflection sites and of the light guiding associated therewith makes it possible to set and/or optimize the reflection conditions at the first, upper and second, lower slotted disk or perforated disk. Moreover, combined with a variation of the distance between the upper and lower slotted disk or perforated disk, it is possible to set the mean, statistically significant and measuring technically effective optical path length in the measuring gas cell and hence to coordinate the gas-measuring device with the wavelength ranges of the gases to be detected with the gas-measuring device without changes being necessary in the overall exterior height of the sensor housing. Furthermore, a variation of the distance between the upper and lower slotted disk or perforated disk brings about a variation in the entry of gas into the measuring gas cell and thus affects the rise time.

The measuring technical properties in the technical design application can be set by selecting the number and size of the openings in the first, upper slotted disk or perforated disk and the number and size of the openings in the second, lower slotted disk or perforated disk, as well as by selecting the distance between the first, upper and second, lower slotted disks, resulting in a ratio between light reflection and signal rise time.

Recesses, which correspond to a projection in the preferably pot-shaped sensor housing, are arranged on the circumference of the first and second slotted disks or perforated disks in another variant of the embodiment according to the present invention to align the slotted or perforated disks with one another.

It is ensured by this combination of projection and recesses that when the slotted disks are assembled with the sensor housing, the first, upper slotted disk and the second, lower slotted disk are arranged in terms of their radial alignment in a reliable manner such that the exit of light into the measuring environment is reproducibly low. Without such a combination of projection and recesses, which leads, as it were, to a securing against rotation, it is otherwise possible that in case of the most unfavorable alignment of the two slotted disks or perforated disks in relation to one another, nearly 50% of the light is emitted through the slotted or perforated disks into the measuring environment.

The variants shown of the embodiment according to the present invention of the arrangement of a first, upper slotted or perforated disk and a second, lower slotted or perforated disk, which is arranged under it at a vertically spaced location from the first, upper slotted or perforated disk, which said arrangement is designed as a gas inlet opening, wherein the openings in the slotted or perforated disks, which openings are preferably designed as slots or perforations, are each arranged offset in relation to one another, represent each independent expressions of the embodiments according to the present invention in themselves.

Besides the independent expressions of the embodiments according to the present invention, combinations of the features of the variants described with one another are also covered by the present invention in a technical embodiment and they in turn represent independent technical expressions according to the present invention in themselves.

Furthermore, embodiments of the essentially round, circular slotted or perforated disks, which have round, circular, elliptical or oval contours or shapes and partly round, circular, elliptical or oval contours or shapes, are also covered by the present invention.

Moreover, the present invention also covers embodiments of the slotted or perforated disks that have, besides the round, circular, elliptical or oval contours or shapes, other geometric shapes as the basic shape, for example, rectangular, square, trapezoid, triangular or polygonal shapes, or have a cloverleaf shape or heart shape as the basic shapes.

The corners of the, for example, rectangular, square, trapezoid, oval, triangular or polygonal shapes are preferably rounded and/or beveled.

In another preferred manner, the outer shape of the slotted or perforated disks and the outer shape of the sensor housing are coordinated with one another. The sensor housing holdingly accommodates the slotted or perforated disks along the circumference. The sensor housing is essentially pot-shaped. The pot shape of the sensor housing is preferably cylindrically round, oval or elliptical and also cubic, rectangular, square or polygonal.

Also covered by the present invention is, in particular, a combination of the alignment of the slotted or perforated disks with one another by means of recesses on the circumference of the first, upper and/or second, lower slotted or perforated disk with projections—corresponding to the first, upper and/or second, lower slotted or perforated disk—in the sensor housing in terms of the outer shape of the slotted or perforated disks as well as in terms of the inner shape of the transparent and gas-permeable openings in the slotted or perforated disks according to the described variants of the embodiment according to the present invention.

The design of the recess may lead to such a design of the shape of the slotted or perforated disk that the recess is no longer recognizable immediately as a distinctive detail in the shaping of the slotted or perforated disk but is included in a free shaping, which is essentially round or circular in terms of the outer shape and/or has a shape corresponding to the shaping of the sensor housing.

Combined with the design of the sensor housing and/or of the measuring gas cell as well as with a recess in the sensor housing, a shape of the slotted circle segments and of the full circle segments, which is heart-shaped or cloverleaf-shaped in some sections, of the slot-like semicircle segments as well as of the star-shaped or radiate, rectangular, star-shaped or radiate, oval or parallel rectangular or oval slots within one of the slotted disks is implemented in a preferred manner in a combined form.

The embodiments and the measuring technical properties thereof in the technical design application can be adapted in the sense of the present invention by selecting the combination of the shapes of the slotted or perforated disks shown in the above-described embodiments with the number and size of the transparent and gas-permeable openings of the first, upper and second, lower slotted or perforated disks and with the distance between the first, upper and second, lower slotted or perforated disks, resulting in a ratio between light reflection and response characteristic.

The embodiments of the slotted or perforated disks described in the embodiment according to the present invention and the variants thereof can be connected to the preferably pot-shaped sensor housing in various ways. A bonded connection or a snap-in connection is preferably provided for this for connecting the slotted disks to the preferably pot-shaped sensor housing. Besides the connection between the sensor housing and the slotted or perforated disks, it is necessary to preset the distance between the two slotted or perforated disks by design measures.

A first and a second deep shoulders, which form a first groove and a second groove, into which the first, upper slotted or perforated disk and/or the second, lower slotted or perforated disk can be inserted and in which these can be positioned and connected to the sensor housing there, are provided for this in the sensor housing on the circumference in the wall in an embodiment of the connection according to the present invention between the slotted or perforated disks to the sensor housing.

The depth of the first deep shoulder in the wall of the sensor housing is selected to be such that this shoulder preferably corresponds essentially to the material thickness of the first, upper slotted or perforated disk, the material thickness of the first, upper slotted disk being preferably selected to be in a range of 0.1 mm to 1.5 mm.

Furthermore, a second deep shoulder is provided, which is arranged in the direction of the vertical central axis of the preferably pot-shaped sensor housing in relation to the first deep shoulder and forms a second groove, which can be inserted into the second, lower slotted or perforated disk and can be positioned there and can be connected to the sensor housing there. The depth of the second deep shoulder in the wall of the sensor housing is selected to be such that it preferably essentially corresponds to the material thickness of the second, lower slotted or perforated disk plus the distance between the first and second slotted or perforated disks, which distance is intended for design reasons.

The material thickness of the first, upper slotted or perforated disk is preferably selected in a range of 0.1 mm to 1.5 mm. The distance between the first and second slotted or perforated disk that is dictated by design reasons is preferably in a range of 0.3 mm to 0.8 mm, and a distance of 0.6 mm is selected in a more preferred manner. The first and second grooves may be prepared in the sensor housing by machining or the sensor housing is provided with the first and second grooves directly during manufacture according to a plastic injection molding process. To assemble the sensor housing with the slotted or perforated disk, the second, lower slotted or perforated disk is, for example, inserted first into the second groove and fastened. The first, upper slotted or perforated disk is subsequently inserted into the first groove and fastened.

The second, lower slotted or perforated disk and the first, upper slotted or perforated disk are preferably connected to the second and first grooves of the wall of the sensor housing by a bonded connection.

Besides the possibility of a bonded connection, a snap-in or clamped connection may be alternatively or additionally provided for connecting the second, lower slotted or perforated disk and the first, upper slotted or perforated disk. The clamped connection is brought about by providing an additional horizontal recess, whose height is made somewhat greater than the material thickness of the first, upper and/or second, lower slotted or perforated disk, in the direction of the outer wall of the sensor housing in the wall of the sensor housing in the first and/or second groove. The diameter of the first and/or second slotted or perforated disk is made slightly larger, for example, in the range of about 0.5 mm to about 2 mm, than the free diameter given by the first and/or second groove for inserting the first and/or second slotted or perforated disk. This causes the slotted or perforated disk to be inserted into the recess at the first and/or second groove during the assembly of the slotted or perforated disks with the sensor housing and to be held at the outer edge of the circumference in the recess such that the slotted or perforated disk is fixed in the wall of the sensor housing in the vertical direction nearly without clearance. The distance between the first, upper and second, lower slotted and perforated disks is thus maintained by design measures within narrow tolerance, which makes it possible to accurately maintain the optical path lengths and improves the measuring technical precision of the sensor.

In a variant of the embodiment according to the present invention of the connection between the slotted or perforated disks with the sensor housing, the slotted or perforated disks are arranged one above the other at spaced locations from one another by means of a spacer element. The spacer element defines the distance between the first, upper and second, lower perforated or slotted disk. A deep shoulder, which forms a groove, into which the second, lower slotted or perforated disk can be inserted during the assembly of the sensor housing and the first and second slotted or perforated disk and in which it can be positioned and connected to the sensor housing there, is provided for this in the sensor housing on the circumference in the wall. The spacer element is positioned on the second, lower slotted or perforated disk and connected to the second, lower slotted or perforated disk and to the sensor housing, and the first, upper slotted or perforated disk is positioned on this spacer element and connected to the spacer element and to the sensor housing.

The depth of the deep shoulder in the wall of the sensor housing is selected to be such that it preferably essentially corresponds to the material thickness of the first and second slotted or perforated disks plus the distance between the first and second slotted or perforated disks, which distance is intended for design reasons and is defined by the spacer element.

A spacer or intermediate ring, which preferably corresponds to the horizontal groove prepared in the wall of the sensor housing, may be used as the spacer element.

The intermediate ring may consist of a solid material, preferably a plastic, over the entire circumference, and one variant of this is represented by an intermediate ring with recesses in some sections, in such a way that the first, upper slotted or perforated disk is held in the vertical position in a punctiform manner by a series of pillar-like individual holding structures, wherein the pillar-like individual holding structures are connected to one another via connection members in a ring-shaped manner.

However, it is also possible, as an alternative or in addition to the intermediate ring, to provide a preferably cylindrical spacer element at the center or at the reference point of the slotted disks, which maintains the first and second slotted disks at spaced locations from one another centrally in the sensor housing.

The cylindrical spacer element is preferably connected to the ring-shaped holding structures via connection members. The holding elements are preferably made of a dimensionally stable material, preferably plastic, for example, by means of a plastic injection molding process and/or by machining and milling.

During assembly, the individual elements can be inserted into the preferably pot-shaped sensor housing, as in the above-described manner, in the sequence second, lower slotted or perforated disk, spacer element, first, upper slotted or perforated disk and connected to said sensor housing. A gas inlet element is formed as a common component in a preferred embodiment from the three components of the second, lower slotted or perforated disk, the spacer element and the first, upper slotted or perforated disk. This gas inlet element is inserted during the assembly with the sensor housing as one element into the groove in the wall of the sensor, aligned and connected to the sensor housing.

In another preferred embodiment, the gas inlet opening comprises a gas inlet element, which comprises an individual slotted or perforated disk due to the preparation or impression of a plurality of recessed contour elements, designed preferably as slotted strips, with transparent and gas-permeable openings present, and two horizontal planes. The two planes form a distance between the plane of the slotted or perforated disk facing the measuring environment and the plane that faces the measuring gas cell due to the introduced contour elements. The two planes are held with one another by the openings preferably formed in the form of slotted strips not being impressed over the full area, which would lead to the punching out of openings, but by the openings of the slotted strips on the circumference being impressed only partly. The disk is made reflective on the underside (lover reflective surfaces). As a result, two horizontal reflection planes with gas inlet openings, directed towards the measuring gas cell, are formed in the gas inlet element on the underside on the basis of a single disk.

In another variant of the embodiment according to the present invention of the connection between the slotted or perforated disks with the sensor housing, the first and/or second slotted or perforated disk is folded back at right angles on the outer circumference into a circular ring, and the folded-back disks form a first, upper pot-shaped element and a second, lower pot-shaped element.

A deep shoulder, which forms a groove, into which the second, lower slotted or perforated disk is inserted during the assembly of the sensor housing and the first and second slotted or perforated disks and in which it is positioned and connected to the sensor housing there, is provided for this in the sensor housing on the circumference in the wall. The first, upper slotted or perforated disk, folded back at right angles, is positioned on the second, lower slotted or perforated disk with the folding directed downwards and connected to the sensor housing. The first, upper slotted or perforated disk is preferably connected to the vertical inner wall of the groove in the sensor housing having the preferred design with the outside of the folded-over, circular ring by means of a bonded connection The second, lower slotted or perforated disk may be similarly folded back at right angles at the outer circumference to form a circular ring in a variant embodiment and the second, lower slotted or perforated disk can be inserted, with the right-angle fold directed upwards, during the assembly of the sensor housing and the second slotted or perforated disk and positioned and connected there to the sensor housing. The first, upper slotted or perforated disk is placed on the folded-back part of the second, lower slotted or perforated disk and connected to the sensor housing.

The second, lower slotted or perforated disk is preferably connected with the outside of the folded-back, circular ring to the vertical inner wall of the groove in the sensor housing having the preferred design by means of a bonded connection. Both the first, upper slotted disk or perforated disk and the second, lower slotted or light passage are folded back at right angles in a special embodiment. The two disks are arranged here in relation to one another such that the folded-back part of the first, upper disk is directed downwards and the folded-back part of the second, lower disk is directed upwards, and the folded disks each form a first, upper pot-shaped element and a second, lower pot-shaped element, whose diameters differ minimally from each other, so that the first pot-shaped element with the downwards directed folded-back part and the second pot-shaped element with the upwards directed folded-back part are fitted together and inserted on the inside into the groove on the sensor housing and are connected there.

The folded-back part of the first, upper disk may surround the folded-back part of the second, lower disk from the outside in the sense of the present invention. In an alternative embodiment of the disks, the arrangement of the folded-back parts in relation to one another may also be selected in the sense of the present invention such that the folded-back part of the second, lower disk surrounds the folded-back part of the first, upper disk from the outside. The first and second pot-shaped elements are preferably assembled by means of a bonded connection into one component.

The definition of a ring folded back at right angles and in a circular pattern at the outer circumference also covers partial right-angle folded-back parts of segments of the outer circumference in the sense of the present invention.

The described variants and embodiments according to the present invention of the connection between the slotted or perforated disks to the sensor housing represent independent expressions of the embodiment according to the present invention each in themselves.

Besides the independent expressions of the embodiments according to the present invention, combinations of the features of the variants described with one another are also covered by the present invention and they in turn represent independent technical expressions according to the present invention in themselves.

Also covered for this are, in particular, the combinations with designs of projections, grooves, recesses in the wall of the sensor housing with recesses and folded-back parts of the slotted and perforated disks in conjunction with spacer elements and snap-in and clamped connections, as well as bonded connections for positioning the slotted and perforated disks in relation to one another and for assembling the slotted and perforated disks into gas inlet elements and for assembling with the sensor housing.

The present invention will be explained in more detail with reference to the drawings attached, where identical reference numbers in the figures designate identical elements. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 2a is a top view of a top disk of an embodiment of a gas inlet opening;

FIG. 2b is a top view of a bottom disk of the embodiment of FIG. 2a;

FIG. 3b is a top view of a bottom disk of the embodiment of FIG. 3a;

FIG. 4b is a top view of a bottom disk of the embodiment of FIG. 4a;

FIG. 5b is a top view of a bottom disk of the embodiment of FIG. 5a;

FIG. 6b is a top view of a bottom disk of the embodiment of FIG. 6a;

FIG. 7b is a top view of a bottom disk of the embodiment of FIG. 7a;

FIG. 8b is a top view of a bottom disk of the embodiment of FIG. 8a;

FIG. 9b is a top view of a bottom disk of the embodiment of FIG. 9a;

FIG. 10b is a top view of a bottom disk of the embodiment of FIG. 10a;

FIG. 11b is a top view of a sensor housing for the gas inlet opening arrangement of FIG. 11a;

FIG. 12b is a top view of a sensor housing for the gas inlet opening arrangement of FIG. 12a;

DESCRIPTION OF THE PREFERRED EMBODIMENTS

Figure 1:
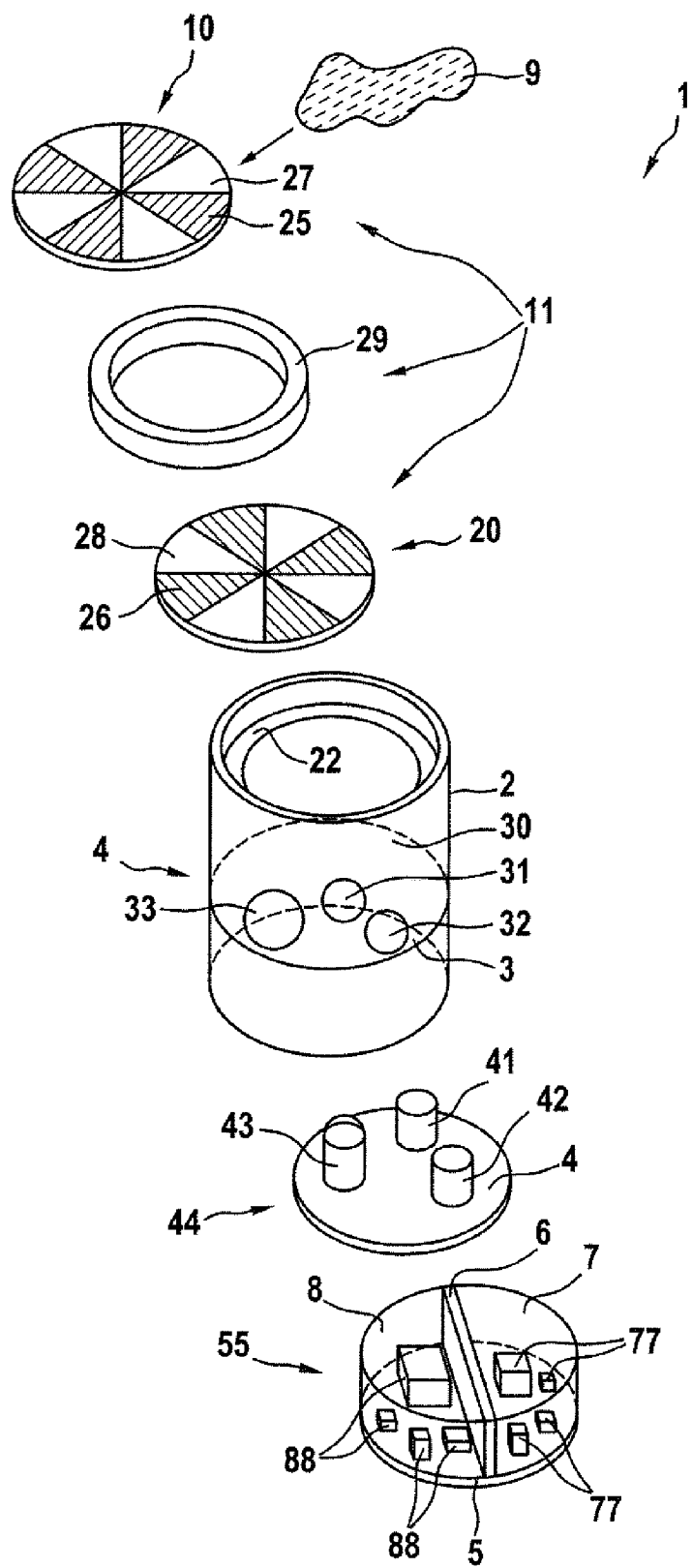
FIG. 1 is an exploded view showing the schematic design of a gas-measuring device according to the invention.

Referring to the drawings in particular, FIG. 1 shows a schematic design of an infrared optical gas-measuring device 1 in the form of a simplified exploded view.

A cylindrical outer housing 2 and a bottom section 3 form together a pot-shaped sensor housing 2. A first light passage 31, a second light passage 32 and a third light passage 33 are present in the bottom section 3. The light passages 31, 32, 33 are designed as sapphire crystals and are connected on the top side or the underside to the bottom section 3. The cylindrical outer housing 2 is designed on the inside and the bottom section 3 is designed on the top side on the surface so as to reflect light in the infrared optical range. An infrared radiation source 43, a first infrared detector 41 and a second infrared detector 42 are arranged under the bottom section 3 in a sensor module 44 on a first holding element 4. A functional module 55 with a second holding element 5 is arranged under the first holding element 4. The functional module 55 contains the first group of electronic components 88 necessary for the operation of the infrared radiation source 43 on the second holding element 5 in a first functional area 8. Functional module 55 contains the second group of electronic components 77 necessary for the operation of the second infrared detector 42 on the second holding element 5 in a second functional area 7. The first functional area 8 and the second functional area 7 are separated gas-tightly from one another by a wall 6. Functional module 55 is arranged under the sensor module 44 and the electronic units 77, 88 are connected via electric connections to the infrared detectors 41, 42 and the infrared radiation source 43. Functional module 55 and the sensor module 44 are inserted together into the sensor housing 2 on the underside under the bottom section 3 such that the first infrared detector 42 is positioned under the second light passage 32 and the infrared radiation source 43 under the third light passage 33.

Furthermore, a first, upper slotted disk 10, a spacer ring 29 and a second, lower slotted disk 20 are present. The first, upper slotted disk 10, spacer ring 29 and the second, lower slotted disk 20 form a gas inlet element 11 as a common assembly unit. Concrete, different embodiments of the slotted disks 10, 20 are shown in more detail in FIGS. 2 through 12 below. On the circumference the slotted disks 10, 20 have an outer edge 16, 17 (FIG. 2), not shown in FIG. 1, consisting of solid material, which brings about the connection of the full circle segments with one another into a stable disk. A second groove 22, into which the gas inlet element 11 is inserted and thus closes the sensor housing 2 on the top side, is provided at the sensor housing 2 on the top side. A measuring gas cell 30, into which a gas 9 flows from a measuring environment, not shown more specifically in FIG. 1, is formed in sensor housing 2 by the bottom section 3, the outer housing 2 and the gas inlet element 11. Nontransparent and gas-impermeable upper full circle segments 25 (each with a reflective lower surface) and transparent and gas-permeable upper slotted circle segments 27 are present in the first, upper slotted disk 10. Non-transparent lower full circle segments 26 (each with a reflective lower surface) and transparent and gas-permeable lower slotted circle segments 28 are present in the second, lower slotted disk 20. The external diameters of the slotted disks 10, 20 are dimensioned in the range of 10 mm to 20 mm and preferably in the range around 15 mm. The first, upper slotted disk 10 is radially offset above the second, lower slotted disk 20 such that the slotted circle segments 27 of the first, upper slotted disk 10 are positioned vertically above the full circle segments 26 of the second, lower slotted disk 20 and full circle segments 25 of the first, upper slotted disk 10 are positioned vertically above the slotted circle segments 28 of the second, lower slotted disk 20.

The gas 9 flows from the measuring environment through the upper slotted circle segments 27 of the first, upper slotted disk 10 and subsequently through the lower slotted circle segments 28 of the second, lower slotted disk 20 into the measuring gas cell 30. The slotted disks 10, 20 are designed on the underside on their surface with the side facing the measuring gas cell 30 so as to reflect light in the infrared optical range. Infrared light is radiated by the infrared radiation source 43 through the third light passage 33 into the measuring gas cell 30 and reflected back into the measuring gas cell 30 for the most part on the reflective surfaces of the first, upper and second, lower slotted disks 10, 20 because of the radial offset of the two slotted disks 10, 20 in relation to one another. A first portion reaches the first infrared detector 41 through the first light passage 31 and the second infrared detector 42 through the second light passage 32. Another portion of the light is reflected once again at the bottom section 3 in the direction of the first, upper and second, lower slotted disks 10, 20, reflected once again there, and it reaches, essentially in the direction of bottom section 3, on this path, partly together with the first portion of the light, the infrared detectors 41, 42 through the light passages 31, 32. The infrared detectors 41, 42 detect the intensity of the light received. Depending on the specific absorption of the light by a gas 9 present in the measuring gas cell 30, the intensity of the light received and hence the signal received from the infrared detectors 41, 42 is attenuated and can be analyzed as an indicator of a specific gas concentration by means of analysis by the electronic unit 77.

FIGS. 2a and 2b show top views of the embodiments of a first, upper slotted disk 10 (FIG. 2a) and of a second, lower slotted disk 20 (FIG. 2b) according to the measuring means shown in FIG. 1. Identical components are designated by the same reference numbers as in FIG. 1. The two slotted disks 10, 20 are shown along a vertical symmetric line 12, which represents the central positioning of the two slotted disks 10, 20 one on top of another. The horizontal symmetric line 13, likewise shown at the first, upper as well as second, lower slotted disks 10, 20, is used to show the radial alignment of the two slotted disks 10, 20 in relation to one another. The intersection of the two symmetric lines 12, 13 forms a center 15. Furthermore, a reference point 14 each is shown at the first, upper slotted disk 10 as well as at the second, lower slotted disk 20. Reference point 14 is located in the same position as the center 15 in this embodiment. The external diameters of the slotted disks 10, 20 are dimensioned such that they are in a range of 10 mm to 20 mm and preferably in a range around 15 mm. The slotted disks 10, 20 are preferably divided into 8 to 16 segments. Four upper full circle segments 25 and four upper slotted circle segments 27 are present in the first, upper slotted disk 10 and four lower full circle segments 26 and four lower slotted circle segments 28 are present in the second, lower slotted disk 20 in the embodiment shown in FIGS. 2a and 2b. A first, outer edge 16 is present at the first, upper slotted disk 10 and an outer edge 17 is present at the second, lower slotted disk 20.

The full circle segments 25, 26 are connected to one another at the center 14 by a center area, not shown more specifically, in a stable manner. The diameter of the first, upper slotted disk 10 and the first, outer edge 16, as well as the diameter of the second, lower slotted disk 10 and the second, outer edge 17 correspond to the diameter of the sensor housing 4 (FIG. 1) and to the dimensions of the second groove 22 (FIG. 1).

The slotted disks 10, 20 are offset radially such that the lower full circle segments 26 are arranged vertically one on top of another with the upper slotted circle segments 27 and the lower slotted circle segments 28 are arranged vertically one on top of another with the upper full circle segments 25.

Figure 3A:
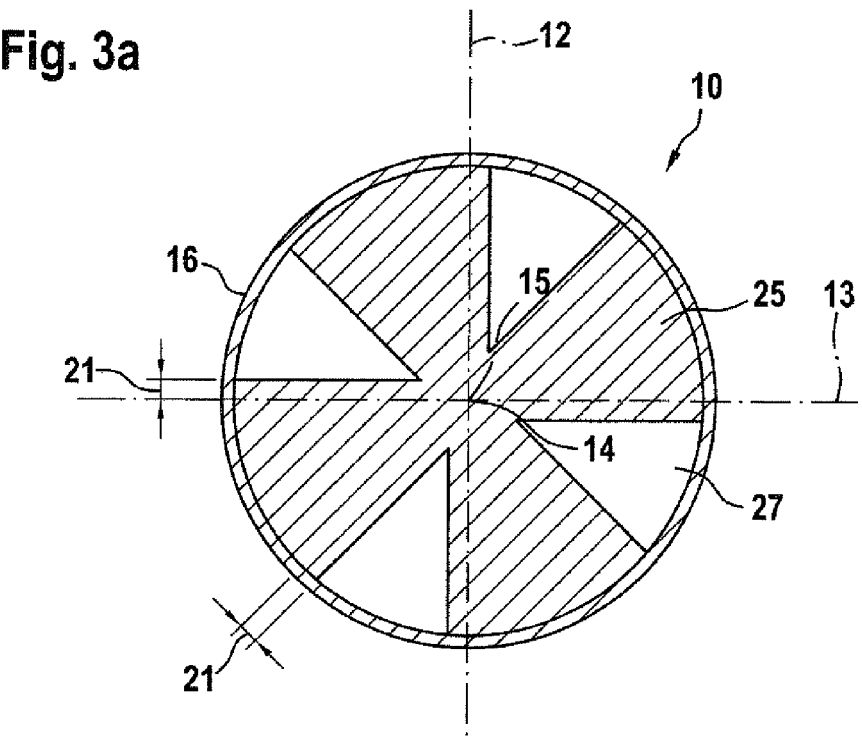
FIG. 3a is a top view of a top disk of an embodiment of a gas inlet opening.
Figure 3B:
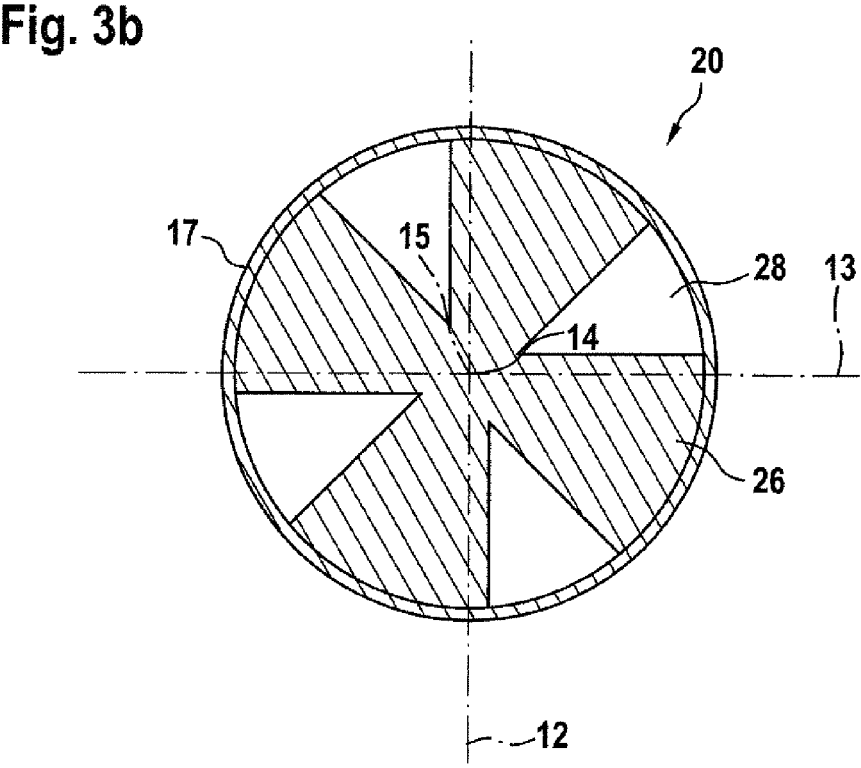

FIGS. 3a and 3b show top views of another embodiment of a first, upper slotted disk 10 (FIG. 3a) and of a second, lower slotted disk 20 (FIG. 3b) in a variation modified compared to FIGS. 2a and 2b for use in a measuring means according to FIG. 1. Identical reference numbers designate in these FIGS. 3a and 3b the same elements as in FIGS. 1, 2a and 2b.

The symmetric lines 12, 13 shown are used to represent the alignment of the two slotted disks 10, 20, as was described in the description of FIGS. 2a and 2b. The intersection of the two symmetric lines 12, 13 forms a center 15. Furthermore, a reference point 14 is shown at the first, upper slotted disk 10 as well as at the second, lower slotted disk 20. Reference point 14 is in the same position as the center 15 in this embodiment. The external diameters of the slotted disks 10, 20 are dimensioned to be in a range of 10 mm to 20 mm and preferably in the range around 15 mm. The slotted disks 10, 20 are divided in this embodiment into 8 segments, namely, 4 full circle segments 25, 26 and 4 slotted circle segments 27, 28. The slotted disks 10, 20 are offset radially such that the lower full circle segments 26 are arranged vertically one on top of another with the upper slotted circle segments 27 and the lower slotted circle segments 28 are arranged vertically one on top of another with the upper full circle segments 25. The areas of the full circle segments 25, 26 of the first, upper slotted disk 10 and of the second, lower slotted disk 20 are made smaller than those of the slotted circle segments 27, 28 of the first, upper slotted disk 10 and of the second, lower slotted disk 20.

This leads to an overlap in terms of area of the upper full circle segments 25 of the first, upper slotted disk 10 with the lower full circle segments 26 of the second, lower slotted disk 20. The overlap in terms of area additionally brings about a stable connection of the full circle segments 25, 26 at center 14.

The overlap increases the incidence angle at which the light, which is reflected from the infrared radiation source 43 (FIG. 1) through the reflective surfaces of the first, upper slotted disk 10 and of the second, lower slotted disk 20, so that almost no portion of the light emitted from the infrared radiation source 43 (FIG. 1) can pass through the slotted circle segments 27, 28 of the first, upper slotted disk 10 and of the second, lower slotted disk 20 in the vertical direction into the measuring environment.

Nearly complete reflection of the infrared optical light emitted by the infrared radiation source 43 (FIG. 1) at the arrangement of the first and second slotted disks 10, 20 even for portions of light that fall on the arrangement of the first and second slotted disks 10, 20 from an essentially non-vertical angle causes that a loss of light onto the measuring environment is avoided and the quantity of light falling on the first and second infrared detectors 41, 42 (FIG. 1) is increased, which leads to an improvement of the signal quality of the first and second infrared detectors 41, 42 (FIG. 1) and hence to improved measuring properties of the gas-measuring device 1 (FIG. 1).

The overlap in terms of area is achieved in this embodiment according to FIGS. 3a and 3b in the form of a symmetrical reduction of the area of the slotted circle segments 27, 28 by shortening the outside length of the cutout of the circle by means of a parallel shifting of the inside lengths of the slotted circle segments 27, 28, which said shifting is directed towards the center of the slotted circle segments 27, 28. An overlap 21 is thus obtained for the full circle segments 25, 26 of the slotted disks 10, 20 on both sides. This bilateral overlap 21 is preferably in a range of 0.2 mm to 0.4 mm and is constant from the center 15 towards the edges 16, 17 of the slotted disks 10, 20.

Figure 4A:
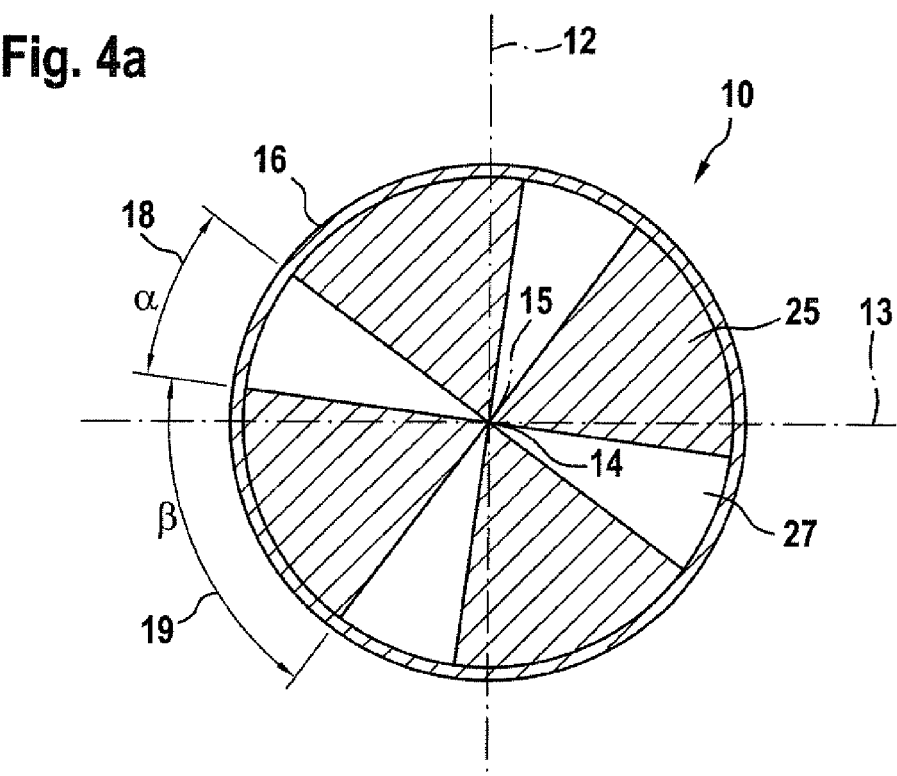
FIG. 4a is a top view of a top disk of an embodiment of a gas inlet opening.
Figure 4B:
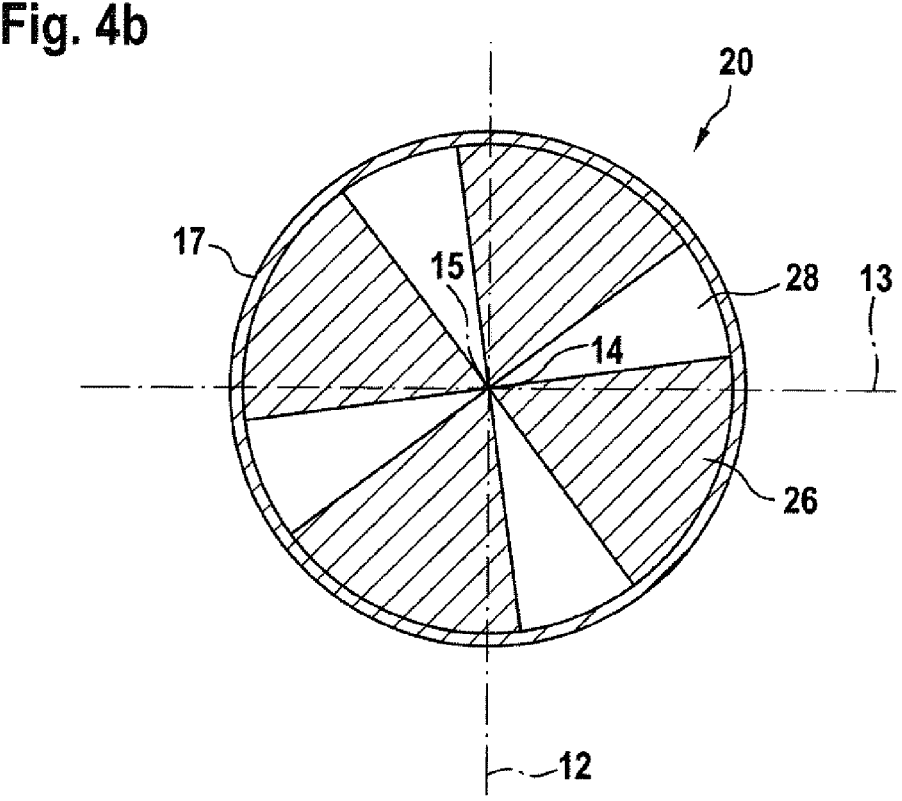

FIGS. 4a and 4b show top views of another embodiment of a first, upper slotted disk 10 (FIG. 4a) and of a second, lower slotted disk (20 (FIG. 4b) in a variation modified compared to FIGS. 2a, 2b and 3 for use in a measuring means according to FIG. 1. Identical reference numbers in these FIGS. 4a, 4b designate the same elements as in FIGS. 1, 2a, 2b, 3a and 3b. The symmetric lines 12, 13 shown are used to represent the alignment of the two slotted disks 10, 20, as is described in the description of FIGS. 2a and 2b. The intersection of the two symmetric lines 12, 13 forms a center 15. Furthermore, a reference point 14 each is shown at the first, upper slotted disk 10 as well as at the second, lower slotted disk 20. Reference point 14 is in the same position as the center 15 in this embodiment. The external diameters of the slotted disks 10, 20 are dimensioned in a range of 10 mm to 20 mm and preferably in the range around 15 mm. The slotted disks 10, 20 are divided in this embodiment into 8 segments, namely, 4 full circle segments 25, 26 and 4 slotted circle segments 27, 28. The slotted disks 10, 20 are offset radially such that the lower full circle segments 26 are arranged vertically one on top of another with the upper slotted circle segments 27 and the lower slotted circle segments 28 are arranged vertically one on top of another with the upper full circle segments 25. The full circle segments 25, 26 are connected to one another at the center 14 by a center area, not shown more specifically, in a stable manner.

The areas of the full circle segments 25, 26 of the first, upper slotted disk 10 and of the second, lower slotted disk 20 are made smaller than those of the slotted circle segments 27, 28 of the first, upper slotted disk 10 and of the second, lower slotted disk 20. This leads to an overlap in terms of area of the upper full circle segments 25 of the first, upper slotted disk 10 with the lower full circle segments 26 of the second, lower slotted disk 20. The overlap in terms of area reduces the portion of light emitted from the measuring gas cell 30 (FIG. 1) into the measuring environment with the advantages described in connection with FIGS. 3a and 3b. The overlap in terms of area is achieved in this embodiment according to FIGS. 4a and 4b by the opening angle 18 of the slotted circle segments 27, 28 being made smaller than the opening angle 19 of the full circle segments 25, 26. The overlap increases from the center 15 towards the edges 16, 17 of the slotted disks 10, 20. Opening angle 18 of the slotted circle segments 27, 28 is made smaller in this embodiment with 8 segments than the opening angle 19 of the full circle segments 25, 26 preferably by an angle difference of 1° to 3°. This leads in this embodiment with 8 segments to an opening angle 19 of the full circle segments 25, 26 of 46° to 48° and to an opening angle of 18 of the slotted circle segments 27, 28 of 42° to 44°.

Figure 5A:
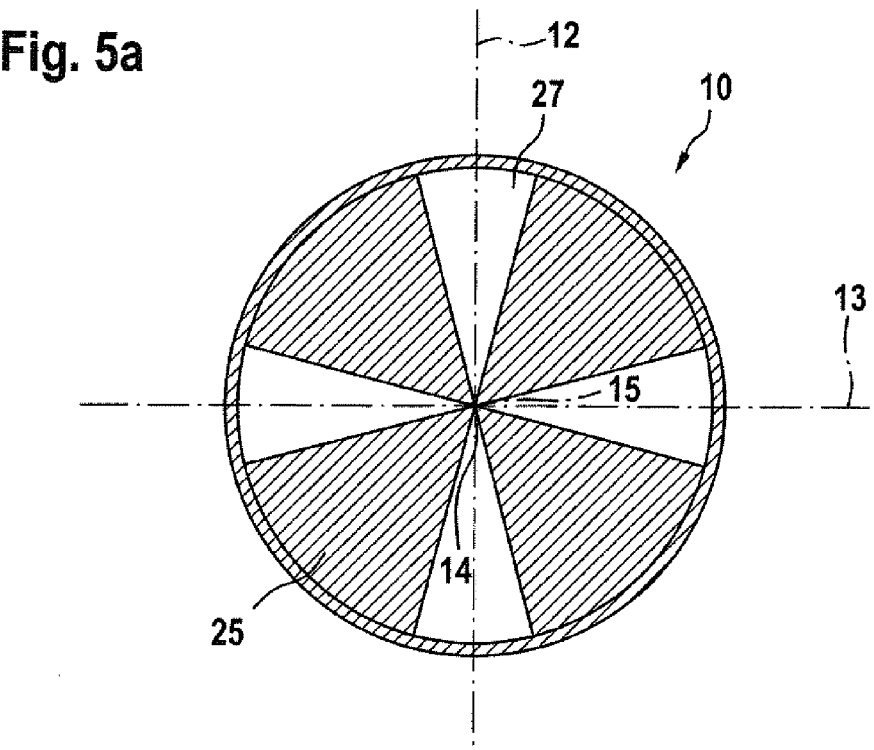
FIG. 5a is a top view of a top disk of an embodiment of a gas inlet opening.
Figure 5B:
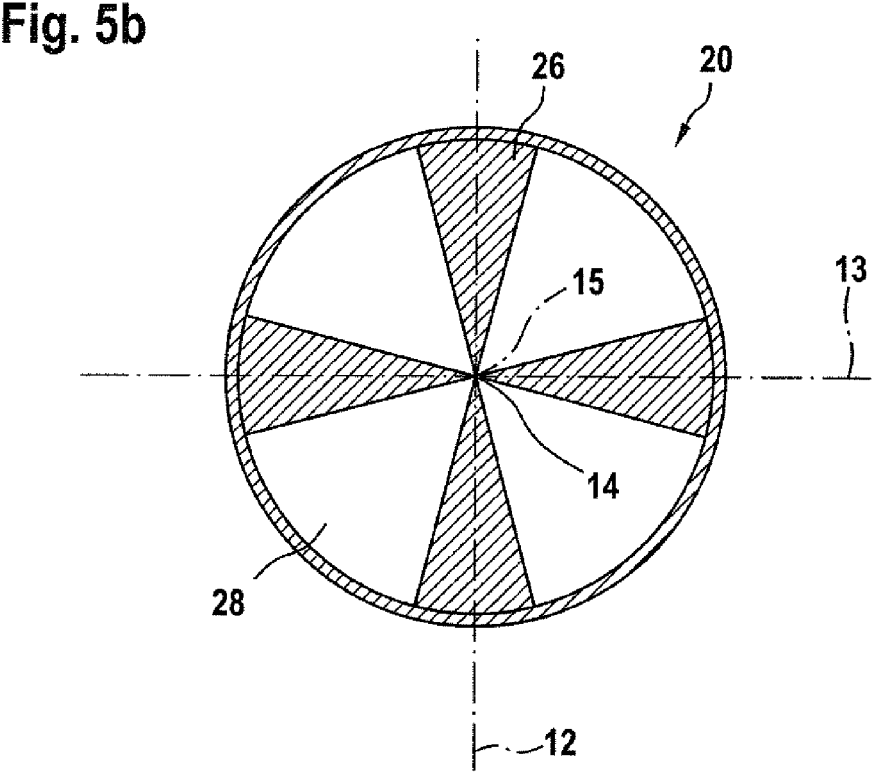

FIGS. 5a and 5b show top views of another embodiment of a first, upper slotted disk 10 (FIG. 5a) and of a second, lower slotted disk 20 (FIG. 5b) in a variation modified compared to FIGS. 2a and 2b for use in a measuring means according to FIG. 1. Identical reference numbers in these FIGS. 5a and 5b designate the same elements as in FIGS. 1, 2a and 2b.

The symmetric lines 12, 13 shown are used to represent the alignment of the two slotted disks 10, 20, as is described in the description of FIGS. 2a and 2b. The intersection of the two symmetric lines 12, 13 forms a center 15. Furthermore, a reference point 14 is shown at the first, upper slotted disk 10 as well as at the second, lower slotted disk 20. Reference point 14 is located in this embodiment in the same position as center 15. The external diameters of the slotted disks 10, 20 are dimensioned in a range of 10 mm to 20 mm and preferably in the range around 15 mm. The slotted disks 10, 20 are divided in this embodiment into 8 segments, namely, 4 full circle segments 25, 26 and 4 slotted circle segments 27, 28. The slotted disks 10, 20 are offset radially such that the lower full circle segments 26 are arranged vertically one on top of another with the upper slotted circle segments 27 and the lower slotted circle segments 28 are located vertically one on top of another with the upper full circle segments 25. The full circle segments 25, 26 are connected to one another at the center by a center area, not shown more specifically, in a stable manner.

The reflective surfaces of the first, upper slotted disk 10, which are formed by the upper full circle segments 25, are made larger in this embodiment according to FIGS. 5a and 5b than the reflective surfaces of the second, lower slotted disk 20, which are formed by the lower full circle segments 26.

A reflective surface of the upper, first slotted disk 10 is thus obtained, which is larger than that of the second, lower slotted disk 20. A larger reflective surface of the upper, first slotted disk 10 increases the optical path length in the measuring gas cell 30 (FIG. 1) without the height of the measuring gas cell 30 (FIG. 1) and hence the measuring gas volume having to be increased. The enlargement of the area of the upper, first slotted disk 10 relative to the area directed towards the infrared radiation source 43 (FIG. 1) is preferably greater by a factor of 1.5 to 3 than the area of the second, lower slotted disk 20 directed towards the infrared radiation source 43 (FIG. 1).

Figure 6A:
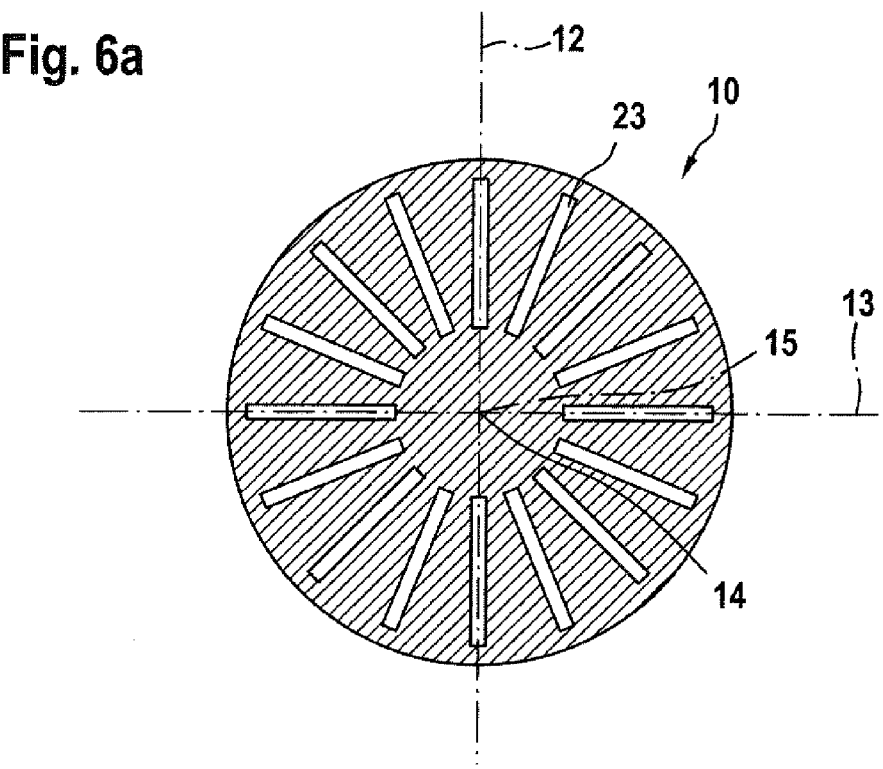
FIG. 6a is a top view of a top disk of an embodiment of a gas inlet opening.
Figure 6B:
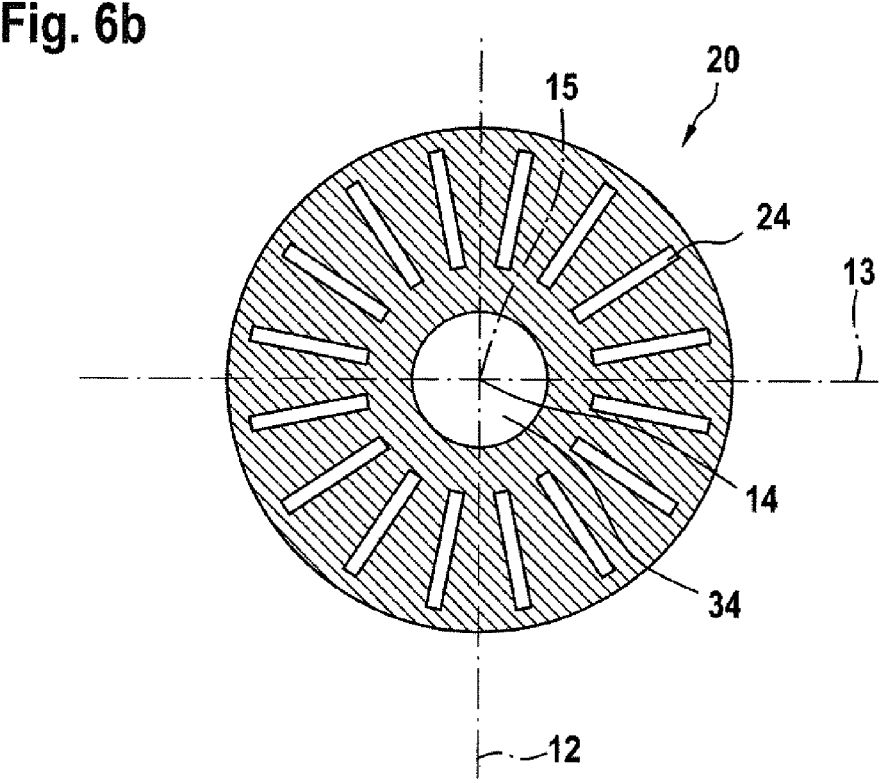

FIGS. 6a and 6b show top views of another embodiment of a first, upper slotted disk 10 (FIG. 6a) and of a second, lower slotted disk 20 (FIG. 6b) in a variation modified compared to FIGS. 2a and 2b for use in a measuring means according to FIG. 1. Identical reference numbers in these figures designate the same elements as in FIGS. 1, 2a and 2b.

The symmetric lines 12, 13 shown are used to represent the alignment of the two slotted disks 10, 20, as it is explained in the description of FIGS. 2a and 2b. The intersection of the two symmetric lines 12, 13 forms a center 15. Furthermore, a reference point 14 is shown at the first, upper slotted disk 10, just as at the second, lower slotted disk 20. Reference point 14 is in the same position as the center 15 in this embodiment.

A plurality of slotted segments 23, 24, preferably a number equaling 12 to 24 slotted segments, each arranged in a star-shaped pattern radially in relation to the reference point 14, are arranged in the first, upper slotted disk 10 and in the second, lower slotted disk 20 in this embodiment according to FIGS. 6a and 6b. The slotted disks 10, 20 are offset radially such that the upper slotted segments 23 of the first, upper slotted disk 10 are not arranged vertically one on top of another with the lower slotted segments 24 of the second, lower slotted disk 20. Thus, there is almost no path for the propagation of light through the two slotted disks 10, 20. Furthermore, the upper slotted segments 23 and the lower slotted segments 24 have different lengths in this embodiment according to FIGS. 6a and 6b, which ensures, besides the radial offset of the slotted disks 10, 20 in relation to one another, that there is no overlap between lower and upper slotted segments 24, 23 in any way. In another preferred manner, the length of the lower slotted segments 24 is made shorter than the length of the upper slotted segments 23, as a result of which a reduced gas inlet area is obtained in the lower slotted disk 20 compared to the upper slotted disk 10. This reduced gas inlet area of the lower slotted disk 20 is compensated by the additional circular inlet opening 34 prepared concentrically with the reference point 14. In case of a preferred diameter of the slotted disks 10, 20 in the range of 10 mm to 20 mm, the lengths of the lower slotted segments 24 are preferably in the range of 2 mm to 6 mm and the lengths of the upper slotted segments 23 are preferably in the range of 4 mm to 9 mm. The widths of the slotted segments 23, 24 are in the range of 0.5 mm to 3 mm. The diameter of passage opening 34 is selected to be in a range of 3 mm to 5 mm.

Figure 7A:
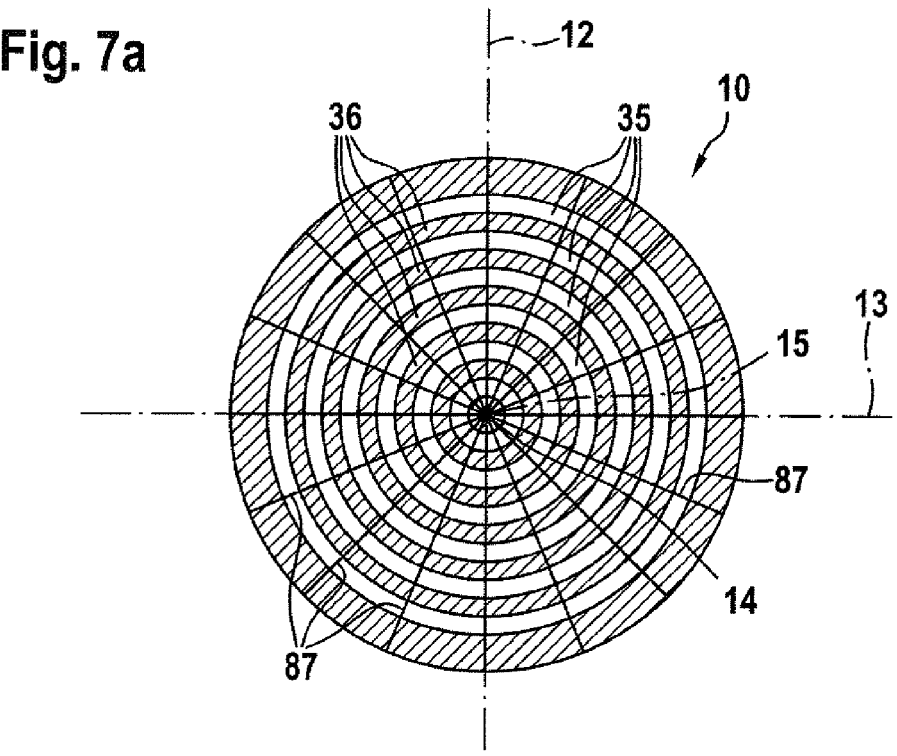
FIG. 7a is a top view of a top disk of an embodiment of a gas inlet opening.
Figure 7B:
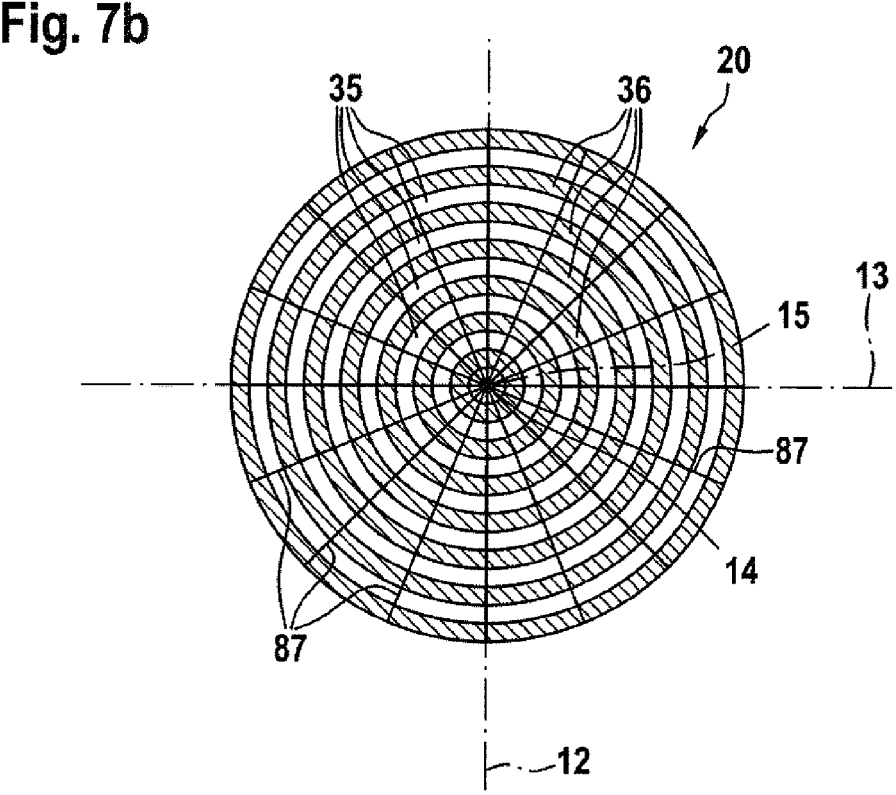

FIGS. 7a and 7b show top views of another embodiment of a first, upper slotted disk 10 (FIG. 7a) and of a second, lower slotted disk 20 (FIG. 7b) in a variation modified compared to FIGS. 2a and 2b for use in a measuring means according to FIG. 1. Identical reference numbers in these FIGS. 7a and 7b designate the same elements as in FIGS. 1, 2a and 2b.

The symmetric lines 12, 13 shown are used to represent the alignment of the two slotted disks 10, 20, as it is explained in the description of FIGS. 2a and 2b. The intersection of the two symmetric lines 12, 13 forms a center 15. Furthermore, a reference point 14 is shown at the first, upper slotted disk 10 as well as at the second, lower slotted disk 20. Reference point 14 is in the same position as center 15 in this embodiment.

A plurality of slotted ring segments 35 are made in this embodiment according to FIGS. 7a and 7b starting concentrically from the reference point 14 alternating with ring segments 36 made of solid material in the slotted disks 10, 20. The external diameters of the slotted disks 10, 20 are dimensioned in a range of 10 mm to 20 mm and preferably in a range around 15 mm. The number of slotted ring segments 35 in the slotted disks 10, 20 is preferably selected in the range 5 to 15 and the width of the slotted ring segments 35 is selected to be in the range of 0.2 mm to 4 mm. The first, upper slotted disks 10 and the second, lower slotted disk 20 are arranged at spaced locations one on top of another, so that the upper slotted ring segment 35 of the first, upper slotted disk 10 and the slotted ring segment 35 of the second, lower slotted disk 20 are shifted in relation to one another radially and concentrically such that slotted ring segments 35 of the lower/upper slotted disk 20, 10 and ring segments 36 of the upper/lower slotted disk 10, 20 are each arranged correspondingly one on top of another. Thus, there is almost no path for the propagation of light through the two slotted disks 10, 20. Web segments 87, which connect the ring segments 36 to one another and guarantee the mechanical stability of the slotted disks 10, 20, are arranged in the slotted disks 10, 20.

Figure 8A:
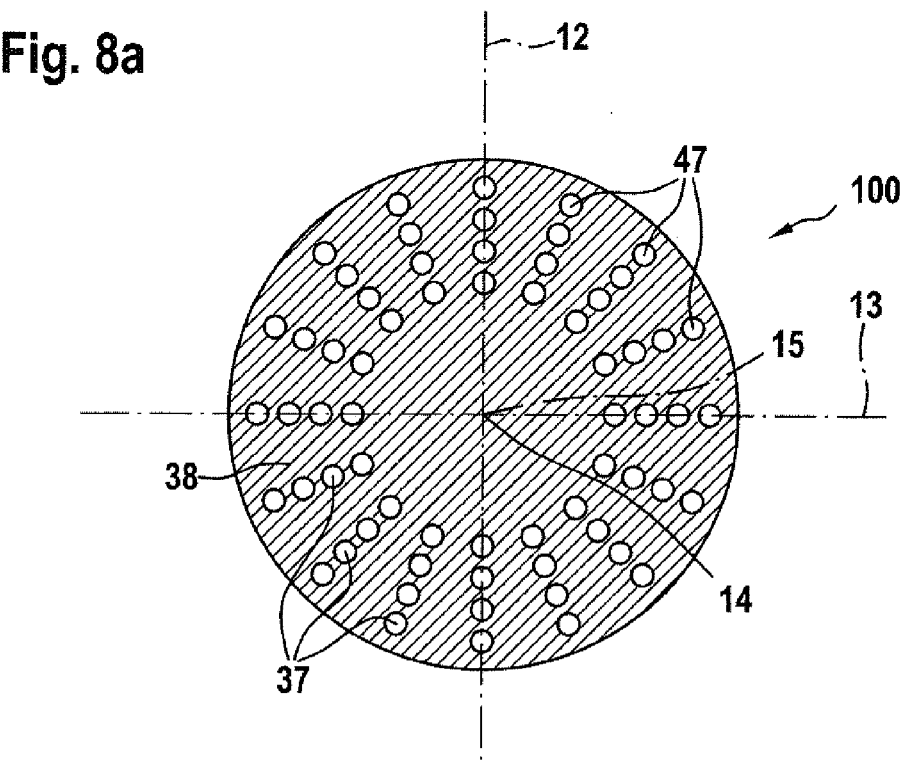
FIG. 8a is a top view of a top disk of an embodiment of a gas inlet opening.
Figure 8B:
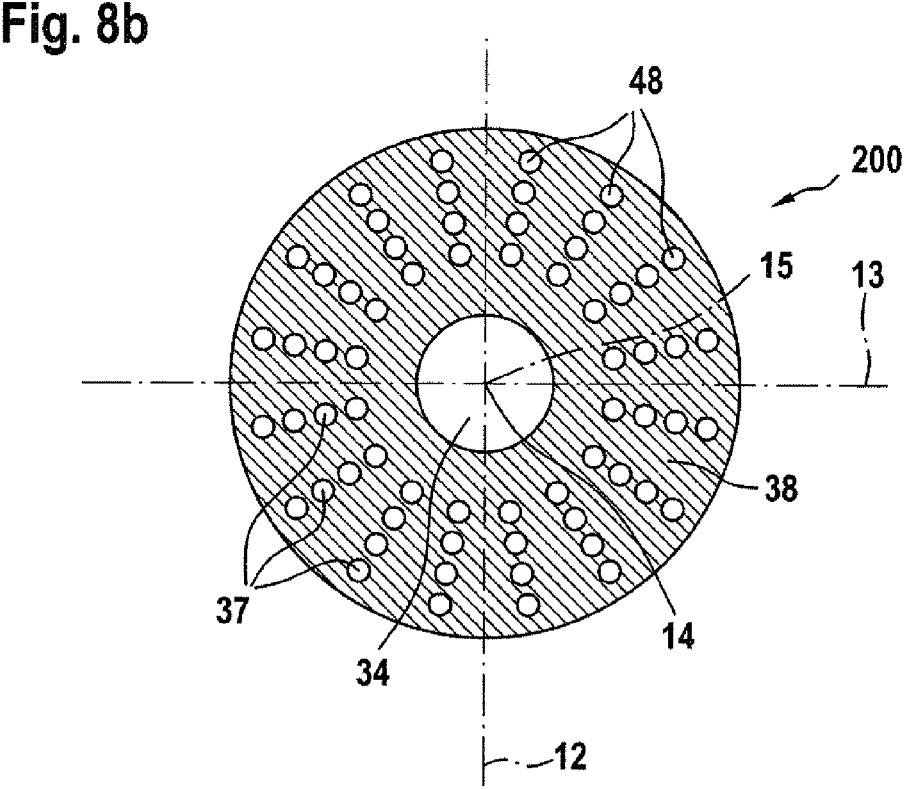

FIGS. 8a and 8b show top views of an embodiment of a first, upper perforated disk 100 (FIG. 8a) and of a second, lower perforated disk 200 (FIG. 8b) for use in a measuring means according to FIG. 1. Identical reference numbers in these FIGS. 8a and 8b designate the same elements as in FIGS. 1, 2a and 2b.

The symmetric lines 12, 13 shown are used to represent the alignment of the two perforated disks 100, 200, as it is explained in the description of the slotted disks 10, 20 for FIGS. 2a and 2b. The intersection of the two symmetric lines 12, 13 forms a center 15. Furthermore, a reference point 14 is shown at the first, upper perforated disk 100 as well as at the second, lower perforated disk 200. Reference point 14 is in the same position as center 15 in this embodiment. The external diameters of the perforated disks 100, 200 are dimensioned in a range of 10 mm to 20 mm and preferably in the range around 15 mm. A plurality of several, circularly arranged perforations 37 are arranged in this embodiment according to FIGS. 8a and 8b starting in a radiate pattern concentrically from the reference point 14 in the first, upper perforated disk 100 as an upper row of perforations 47 and in the second, lower perforated disk 200 as a lower row of perforations 48. The rest of the perforated disks 100, 200 is formed by solid material 38 that is not transparent to light. The number of rows of perforations 47 is preferably in the range of 12 to 24. The diameters of the perforations 37 are in a range of 1 mm to 3 mm. The first, upper perforated disk 100 and the second, lower perforated disk 200 are arranged at spaced locations one on top of another such that the perforations 37 of the first, upper perforated disk 100 in the upper rows of perforations 47 and the perforations 37 of the second, lower perforated disk 200 in the lower rows of perforations 48 are arranged radially offset in relation to one another such that the perforations 37 of the first, upper perforated disk 100 are not arranged vertically one on top of another with the perforations 37 of the second, lower perforated disk 200.

Thus, there is hardly any path for the propagation of light through the two perforated disks 100, 200.

Figure 9A:
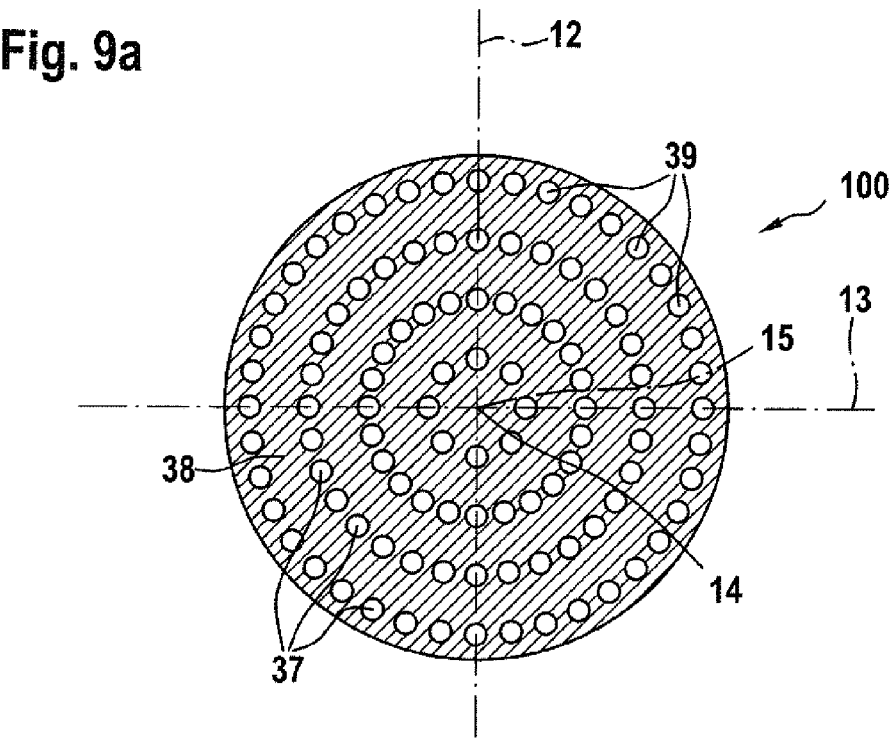
FIG. 9a is a top view of a top disk of an embodiment of a gas inlet opening.
Figure 9B:
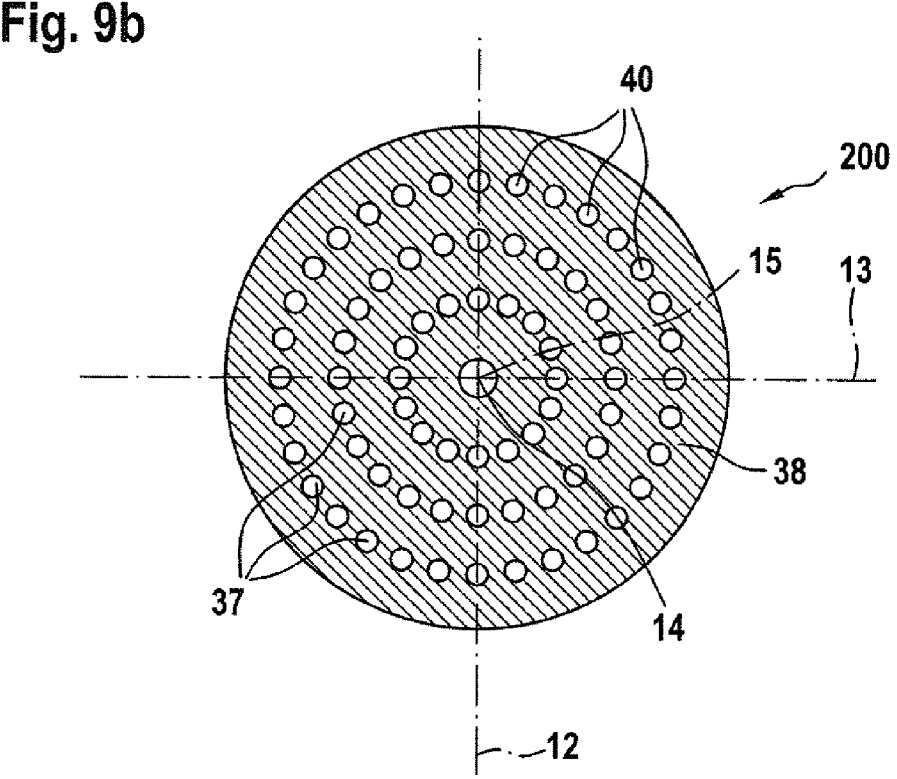

FIGS. 9a and 9b show top views of another embodiment of a first, upper perforated disk 100 (FIG. 9a) and of a second, lower perforated disk 200 (FIG. 9b) for use in a measuring means according to FIG. 1. Identical reference numbers in these FIGS. 9a and 9b designate the same elements as in FIGS. 1, 2a and 2b. The symmetric lines 12, 13 shown are used to represent the alignment of the two perforated disks 100, 200, as is explained in the description of the slotted disks 10, 20 for FIGS. 2a and 2b. The intersection of the two symmetric lines 12, 13 forms a center 15. Furthermore, a reference point 14 is shown at the first, upper perforated disk 100 as well as at the second, lower perforated disk 200. Reference point 14 is in the same position as center 15 in this embodiment. The external diameters of the perforated disks 100, 200 are dimensioned in a range of 10 mm to 20 mm and preferably in the range around 15 mm. A plurality of several perforations 37 arranged circularly in rings 39, 40 are arranged in this embodiment, starting concentrically from the reference point 14 in the first, upper perforated disk 100 and in the second, lower perforated disk 200. The rest of the perforated disks 100, 200 is made of a solid material 38 that is not transparent to light. The number of rings 39, 40 in the perforated disks 100, 200 is preferably selected in the range of 4 to 12. The diameters of the perforations 37 are in a range of 1 mm to 3 mm.

The first, upper perforated disk 100 and the second, lower perforated disk 200 are arranged at spaced locations one on top of another such that the perforations 37 of the first, upper perforated disk 100 in the upper rings 39 and the perforations 37 of the second, lower perforated disk 200 in the lower rings 40 are arranged in parallel to one another.

The arrangement is designed, furthermore, such that the upper rings 39 with the perforations 37 of the first, upper perforated disk 100 and the lower rings 40 with the perforations 37 of the second, lower perforated disk 200 are offset radially in relation to one another such that the perforations 37 of the first, upper perforated disk 100 are not arranged vertically one on top of another with the perforations of the second, lower perforated disk 200.

The arrangement is designed, furthermore, such that the perforations 37 of the first, upper perforated disk 100 and the perforations 37 of the second, lower perforated disk 200 are shifted in relation to one another radially and concentrically such that the perforations 37 of the upper perforated disk 100 are not arranged correspondingly one on top of another with the perforations 37 of the lower perforated disk 200. Thus, there is almost no path for the propagation of light through the two perforated disks 100, 200.

Figure 10A:
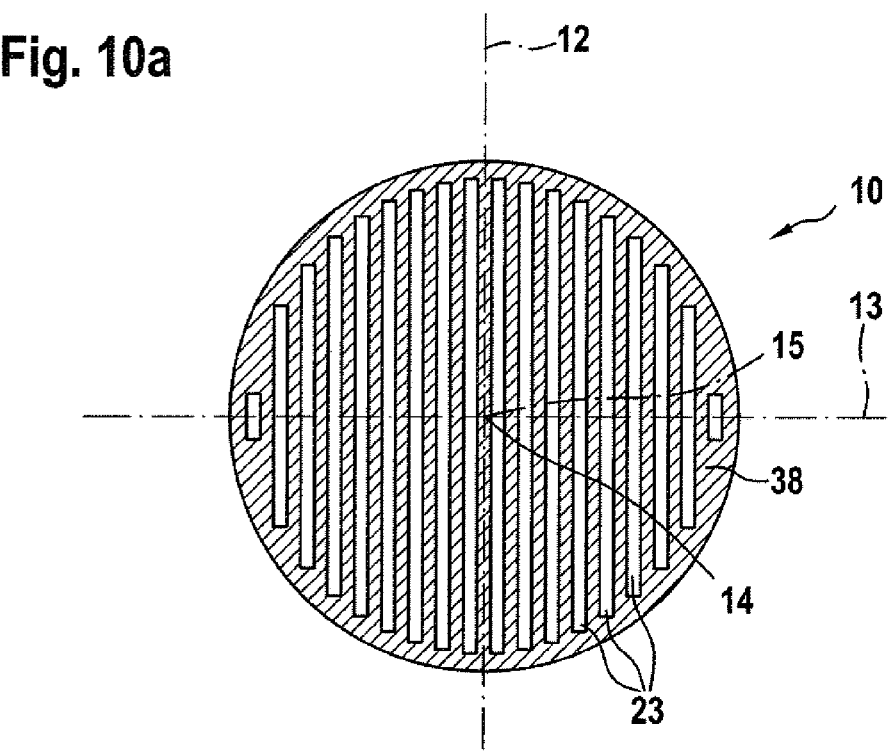
FIG. 10a is a top view of a top disk of an embodiment of a gas inlet opening.
Figure 10B:
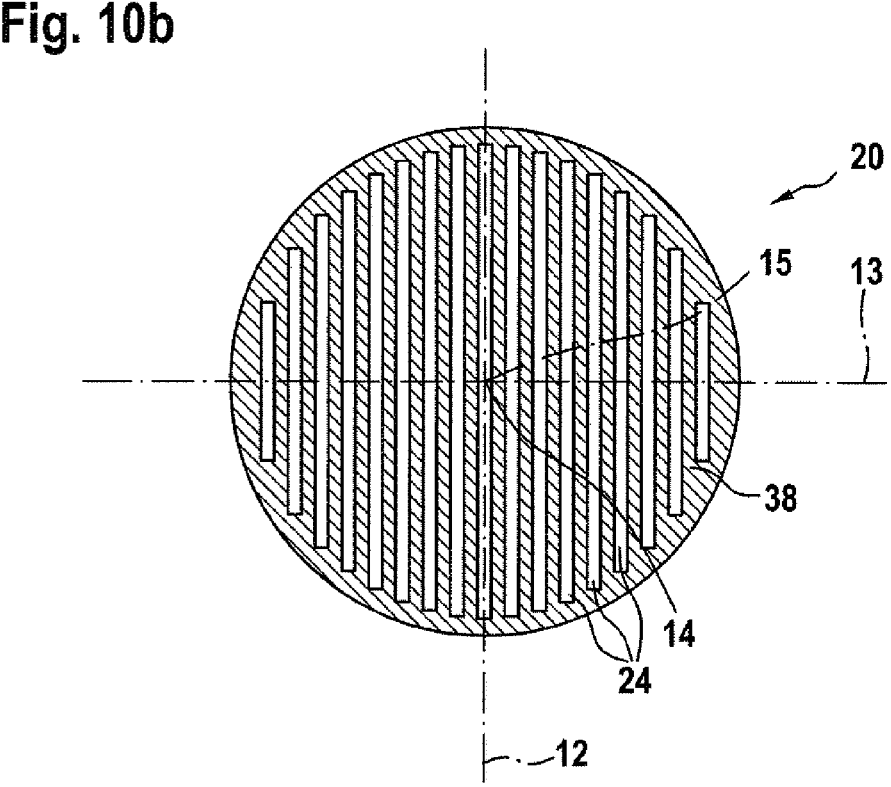

FIGS. 10a and 10b show top views of another embodiment of a first, upper slotted disk 10 (FIG. 10a) and of a second, lower slotted disk 20 (FIG. 10b) in a variation modified compared to FIGS. 2a and 2b for use in a measuring means according to FIG. 1. Identical reference numbers in these FIGS. 10a and 10b designate the same elements as in FIGS. 1, 2a and 2b.

The symmetric lines 12, 13 shown are used to represent the alignment of the two slotted disks 10, 20, as is explained in the description for FIGS. 2a and 2b. The intersection of the two symmetric lines 12, 13 forms a center 15. Furthermore, a reference point 14 is shown at the first, upper slotted disk 10 as well as at the second, lower slotted disk 20. Reference point 14 is located in the same position as the center 15 in this embodiment.

A plurality of parallel slotted segments 23, 24, preferably in a number of 6 to 20 slotted segments 23, 24 with a preferred width of 0.1 mm to 0.6 mm, are arranged each in the first, upper slotted disk 10 and in the second, lower slotted disk 20 in this embodiment according to FIGS. 10a and 10b. The rest of the slotted disks 10, 20 is made of solid material 38 that is not transparent to light.

The upper slotted segments 23 are offset in parallel along the horizontal symmetric line 13 in relation to the lower slotted segments 24 such that the upper slotted segments 23 of the first, upper slotted disk 10 are not arranged vertically one on top of another with the lower slotted segments 24 of the second, lower slotted disk 20. Thus, there is almost no path for the propagation of light through the two slotted disks 10, 20.

Figure 11A:
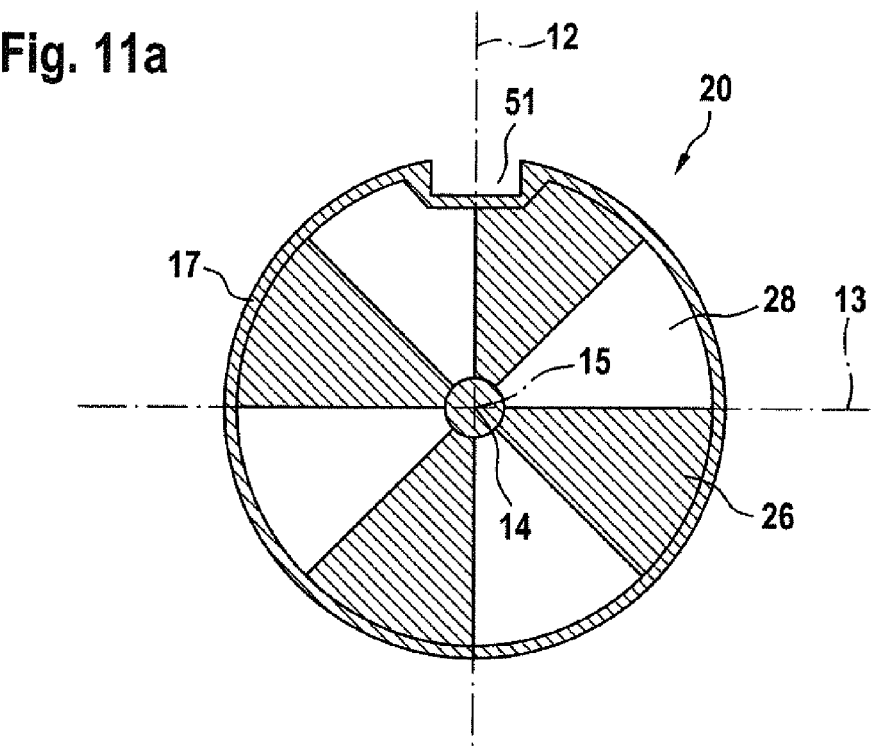
FIG. 11a is a top view of the bottom disk of an arrangements of a gas inlet opening.
Figure 11B:
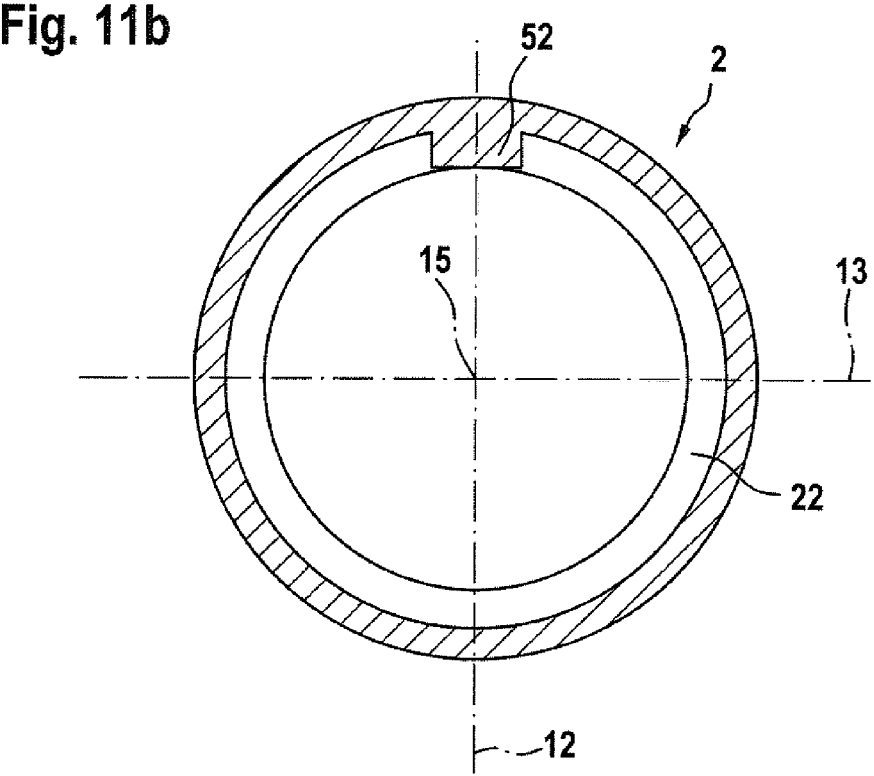

FIGS. 11a and 11b show top views of an arrangement of slotted disks 10, 20 (FIG. 11a) with the outer housing 2 (FIG. 11b). Shown are the lower slotted disk 20 (FIG. 11a) with lower full circle segments 26 and lower slotted circle segments 28 and the outer housing 2 (FIG. 11b) with a second groove 22, into which the lower slotted disk 20 is inserted. The second, lower slotted disk 20 is divided in this embodiment into 8 segments, namely, four full circle segments 26 and four slotted circle segments 28. The symmetric lines 12, 13 shown are used to represent the alignment of the first, upper slotted disk 10 (FIG. 1) and of the second, lower slotted disk 20 in relation to one another and with the outer housing 2, as it is explained in the description for FIGS. 2a and 2b. The intersection of the two symmetric lines 12, 13 forms a center 15, which is used as a reference point 14 for the symmetrical arrangement of the lower full circle segments 26 and the lower slotted circle segments 28. The radial positioning and securing against rotation about the center 15 between the second, lower slotted disk 20 and the outer housing 2, as well as the radial positioning and securing against rotation between the first, slotted disk—not shown in FIGS. 11a and 11b—and the outer housing 2 is guaranteed by the combination of a projection 52 in the outer housing 2 and corresponding recesses 51 arranged on the circumference of the slotted disks (10, 20).

Figure 12A:
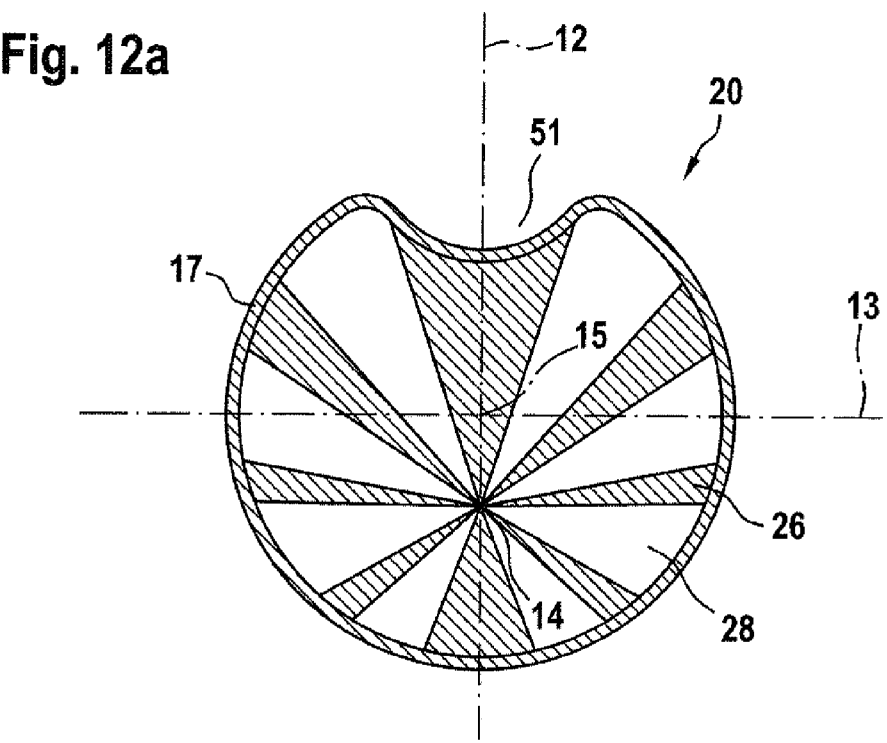
FIG. 12a is a top view of the bottom disk of an arrangements of a gas inlet opening.
Figure 12B:
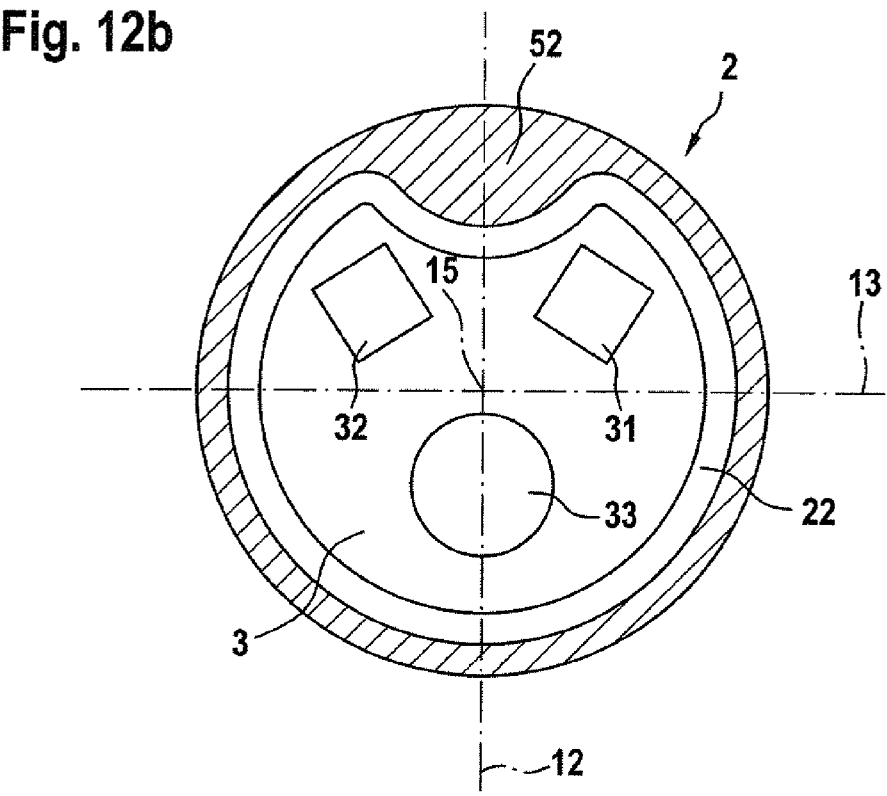

FIGS. 12a and 12b show top views of another arrangement of slotted disks 10, 20 with outer housing 2 and bottom section 3. Shown are the lower slotted disk 20 (FIG. 12a) with lower full circle segments 26 and lower slotted circle segments 28 and the outer housing 2 (FIG. 12b) with a second groove 22, into which the lower slotted disk 20 is inserted with the second, outer edge 17. Furthermore, the light passages 31, 32, 33 present in the bottom section 3 are schematically shown in the top view of the outer housing 2 (FIG. 12b).

The symmetric lines 12, 13 shown are used to represent the alignment of the first, upper slotted disk 10 (FIG. 1) and of the second, lower slotted disk 20 in relation to one another and with the outer housing 2, as it is explained in the description for FIGS. 2a and 2b. The second, lower slotted disk 20 is divided in this embodiment into 8 segments, namely, four full circle segments 26 and four slotted circle segments 28. The intersection of the two symmetric lines 12, 13 forms a center 15. Furthermore, a reference point 14 for arranging the lower full circle segments 26 and the lower slotted circle segments 28 in the second, lower slotted disk 20 is shown, which reference point is offset laterally from the center 15 towards the circumference of the second, lower slotted disk 20. The same reference point 14 is selected for the arrangement of the upper full circle segments 25 (FIG. 1) and of the upper slotted circle segments 27 (FIG. 1) in the first, upper slotted disk 10 (FIG. 1) as for the arrangement of the lower full circle segments 26 and of the lower slotted circle segments 28 in the second, lower slotted disk 20.

Furthermore, a bottom section 3 with light passages 31, 32, 33 is shown. The position of the reference point 14 deviating from the center 15 allows for the fact that the third light passage 33, under which the infrared radiation source 43 (FIG. 1) is arranged, is likewise not arranged in the center of bottom section 3. The first and second light passages 31, 32, under which the infrared detectors 41, 42 (FIG. 1) are arranged, are likewise arranged offset in relation to the center in bottom section 3. The radiation of the light of the infrared radiation source 43 (FIG. 1) through the third light passage 33 and the entry of light onto the infrared detectors 41, 42 (FIG. 1) through the first and second light passages 31, 32 as well as the design of the optical paths with reflections and reflection angles at the first, upper slotted disk 10 (FIG. 1), at the wall 6 (FIG. 1) of the outer housing 2, at the bottom section 3 and at the second, lower slotted disk 20 is substantially affected by the arrangement of the light passages 31, 32, 33 in bottom section 3.

The design of the slotted disks 10, 20 with the circle segments (25, 26, 27, 28) (FIG. 1) symmetrically to the reference point 14 and asymmetrically to the center 15 is a suitable design means to optimize the optical paths and path lengths for the task of measurement, especially as an adaptation to the wavelengths of the gases to be measured. The bottom section 3 with the light passages 31, 32, 33, with the infrared detectors 41, 42 (FIG. 1) arranged under it and with the infrared radiation source 43 (FIG. 1) arranged under it and the slotted disks 10, 20 are thus correspondingly coordinated with one another.

The radial positioning and securing against rotation about the center 15 between the second, lower slotted disk 20 and the outer housing 2, as well as the radial positioning and securing against rotation between the first, lower slotted disk—not shown in FIGS. 12a and 12b—and the outer housing 2 is guaranteed by the combination of a projection 52 in the outer housing 2 and corresponding recesses 51 arranged on the circumference of the slotted disks (10, 20). The position of the recesses 51 in the slotted disks 10, 20 in relation to the reference point 14 and the size thereof are selected to be such that the reflection of the light radiation is reduced as little as possible. Location of the recess 51 opposite the third light passage 33 in the bottom section 3 with the infrared radiation source 43 (FIG. 1) located under it has proved to be advantageous in measuring experiments. The shape of the recess 51 and of the projection 52 is coordinated with the exterior space conditions of the measuring means 1 (FIG. 1) and the optimization of the optical paths and path lengths is coordinated with the measuring task.

Figure 13:
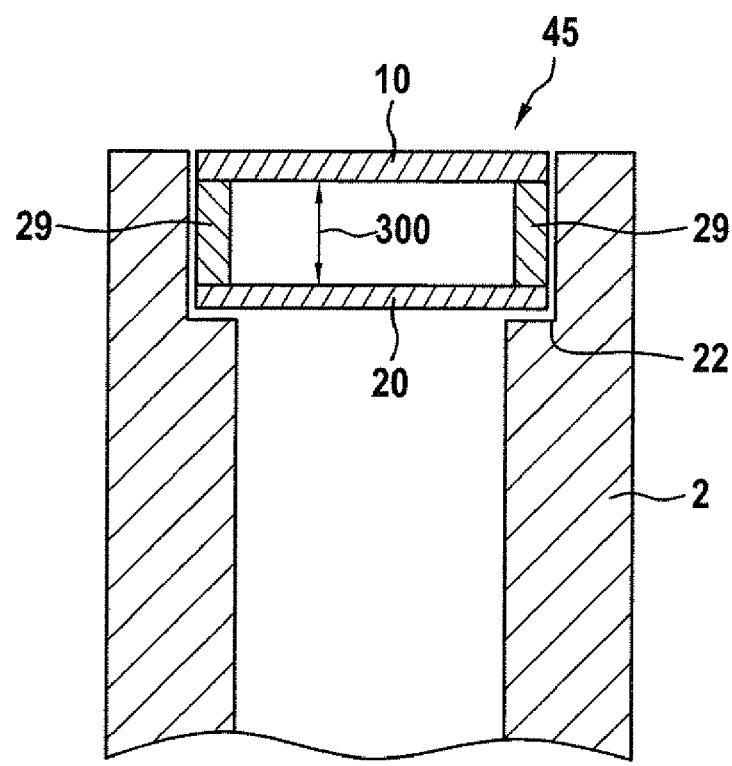
FIG. 13 is a cross sectional view showing an embodiment of an assembly comprising a gas inlet opening and a sensor housing.

FIG. 13 shows as a cross-sectional view an arrangement for assembling an outer housing 2 with a first, upper slotted disk 10 and a second, lower slotted disk 20 and with a spacer ring 29. The outer housing 2 is provided with a second groove 22 on the top side on the circumference. Projections 52 (FIG. 11) in the outer housing 2 and corresponding recesses 51 (FIG. 11) in the slotted disks 10, 20 for radially positioning the slotted disks 10, 20 and securing them against rotation are not shown in this cross-sectional view in FIG. 13. Spacer ring 29 is connected with the first, upper slotted disk 10 and the second, lower slotted disk 20 as a gas inlet module 45 into a common component and forms a space 300 between the first, upper slotted disk 10 and the second, lower slotted disk 20. The gas inlet module 45 is inserted into the second groove 22 on the outer housing 2 in an accurately fitting manner and is connected to same.

Figure 14:
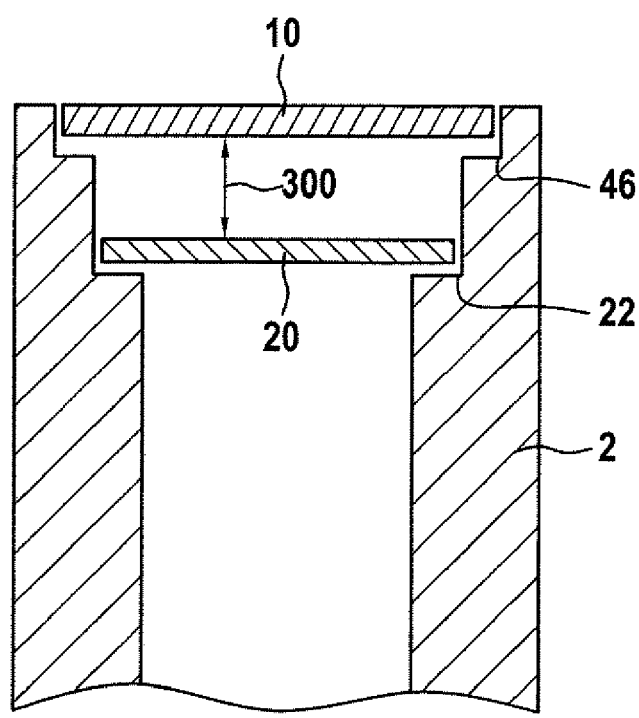
FIG. 14 is a cross sectional view showing another embodiment of an assembly comprising a gas inlet opening and a sensor housing.

FIG. 14 shows as a cross-sectional view an arrangement for assembling an outer housing 2 with a first, upper slotted disk 10 and with a second, lower slotted disk 20.

The outer housing 2 is provided with a second groove 22 and a first groove 46 on the top side on the circumference. Projections 52 (FIG. 11) in the outer housing 2 and corresponding recesses 51 (FIG. 1) in the slotted disks 10, 20 for radially positioning the slotted disks 10, 20 and securing them against rotation are not shown in this cross-sectional view in FIG. 14. The second, lower slotted disk 20 is inserted into the second groove 22 and fastened, and the first, upper slotted disk is inserted into the first groove 46 and fastened. The vertical distance 300 between the first, upper slotted disk 10 and the second, lower slotted disk 20 is predetermined by the vertical distance between the second groove 22 and the first groove 46 and the material thickness of the second slotted disk 20.

Figure 15:
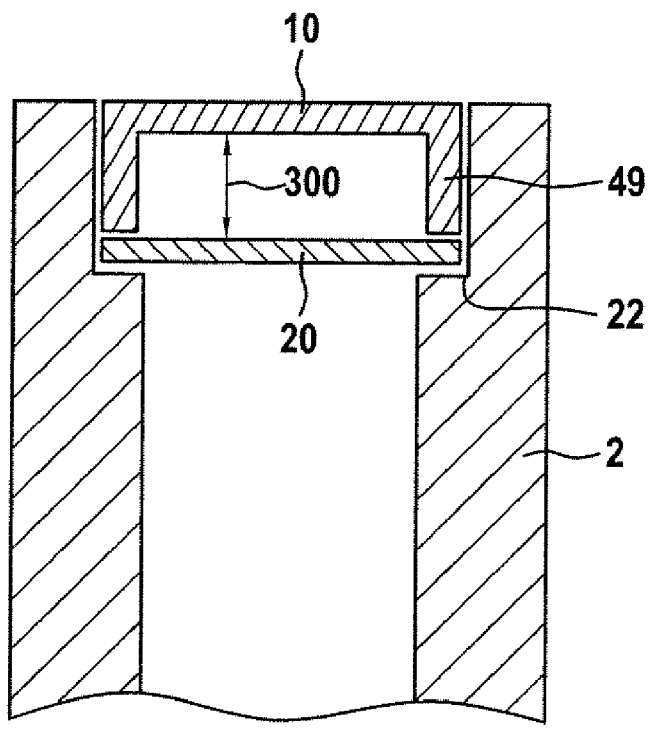
FIG. 15 is a cross sectional view showing another embodiment of an assembly comprising a gas inlet opening and a sensor housing.

FIG. 15 shows as a cross-sectional view another arrangement for assembling an outer housing 2 with a first, upper slotted disk 10 and a second, lower slotted disk 20. The design of the outer housing 2 corresponds to the design according to FIG. 13. The outer housing 2 is provided with a second groove 22 on the top side on the circumference. Projections 52 (FIG. 11) in the outer housing 2 and corresponding recesses 51 (FIG. 11) in the slotted disks 10, 20 for radially positioning the slotted disks 10, 20 and securing them against rotation are not shown in this cross-sectional view in FIG. 15. The first, upper slotted disk 10 is folded back at right angles. The folded-back part forms a first edge 49, which forms a distance 300 between the first, upper slotted disk 10 and the second, lower slotted disk 20. The second, lower slotted disk 20 is inserted into the second groove 22 and fastened. The first, upper slotted disk 10 is placed with the edge 49 facing downward into the second groove 22 on the second, lower slotted disk 20 and connected to the outer housing 2.

Figure 16:
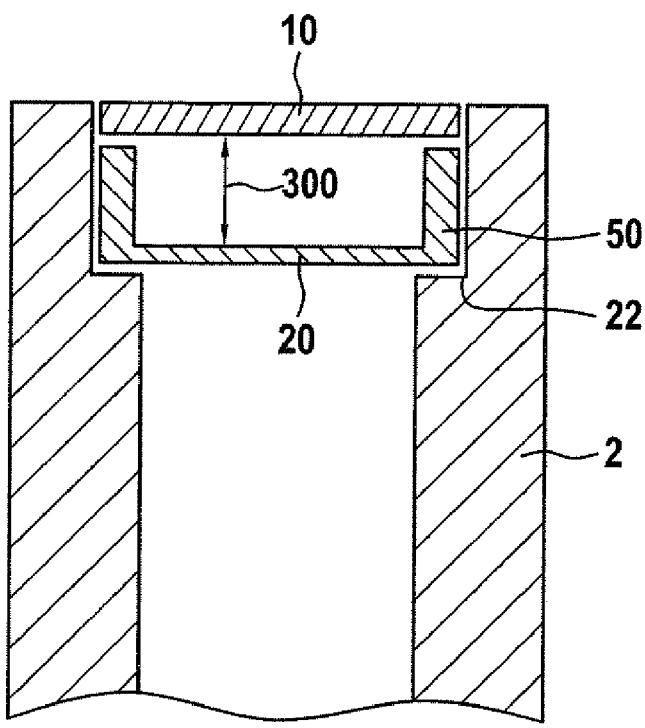
FIG. 16 is a cross sectional view showing another embodiment of an assembly comprising a gas inlet opening and a sensor housing.

FIG. 16 shows in a cross-sectional view another arrangement for assembling an outer housing 2 with a first, upper slotted disk 10 and a second, lower slotted disk 20. The design of the outer housing 2 corresponds to the design according to FIG. 13. The outer housing 2 is provided with a second groove 22 on the top side on the circumference. Projections 52 (FIG. 11) in the outer housing 2 and corresponding recesses 51 (FIG. 11) in the slotted disks 10, 20 for radially positioning the slotted disks 10, 20 and securing them against rotation are not shown in this cross-sectional view in FIG. 16. The second, lower slotted disk 20 is folded back at right angles. The folded-back part forms a second edge 50, which forms a space 300 between the first, upper slotted disk 10 and the second, lower slotted disk 20. The second, lower slotted disk 20 is placed with the edge 50 into the second groove 22 and is connected to the outer housing 2. The first, upper slotted disk 10 is arranged such that it lies on edge 50.

The first and second slotted disks 10, 20 are connected to the outer housing 2.

Figure 17:
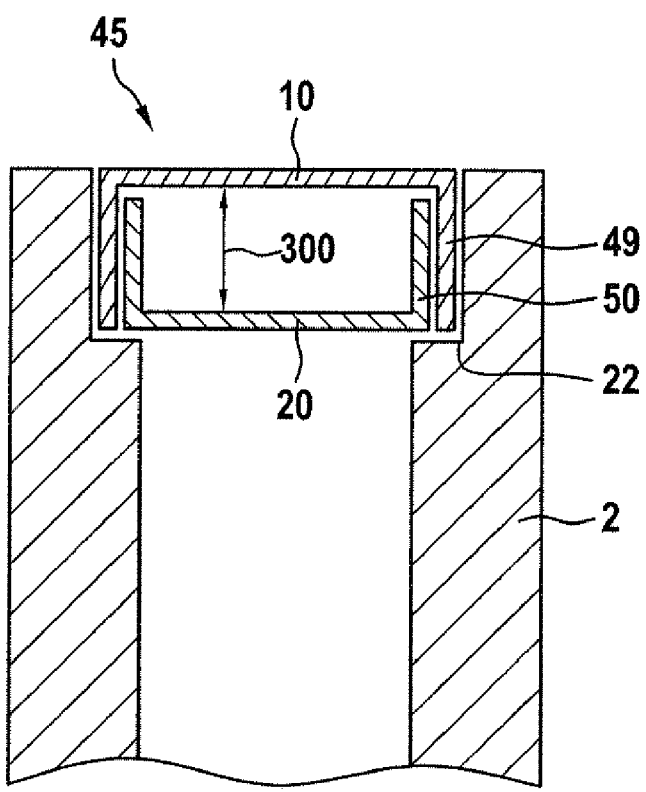
FIG. 17 is a cross sectional view showing another embodiment of an assembly comprising a gas inlet opening and a sensor housing.

FIG. 17 shows in a cross-sectional view another arrangement for assembling an outer housing 2 with a first, upper slotted disk 10 and a second, lower slotted disk 20. The design of the outer housing 2 corresponds to a combination of the designs according to FIG. 15 and FIG. 16. The outer housing 2 is provided with a second groove 22 on the top side on the circumference. Projections 52 (FIG. 11) in the outer housing 2 and corresponding recesses 51 (FIG. 11) in the slotted disks 10, 20 for radially positioning the slotted disks 10, 20 and securing them against rotation are not shown in this cross-sectional view in FIG. 17. The first, upper slotted disk 10 and the second, lower slotted disk 20 are folded back at right angles. The folded-back parts form a first edge 49 on the first, upper slotted disk 10 and a second edge 50 on the second, lower slotted disk 20, which together form a space 300 between the first, upper slotted disk 10 and the second, lower slotted disk 20. The second, lower slotted disk 20 is placed with the upwards directed edge 50 into the second groove 22. The first, upper slotted disk 10 is placed on edge 50 such that it lies on in with the downwards directed edge 49, the first edge 49 surrounding the edge 50 from the outside in this embodiment. In an alternative embodiment of the slotted disks 10, 20, the arrangement of the edges 49, 50 in relation to one another may also be selected in the sense of the present invention such that the second edge 50 surrounds the first edge 49 from the outside. Edges 49, 50 are dimensioned such that, lying one inside the other, they together represent the distance 300. The first and second slotted disks 10, 20 are connected to one another via the edges 49, 50 lying one inside the other to form a gas inlet module 45. Due to this design of the gas inlet module 455, increased wall thickness is obtained to embody the distance 300 with increased mechanical strength, and the material thickness of the first and second slotted disks 10, 20 can be selected to be small at the same time. The first and second slotted disks 10, 20 are connected as a gas inlet module 45 to the outer housing 2.

Figure 18:
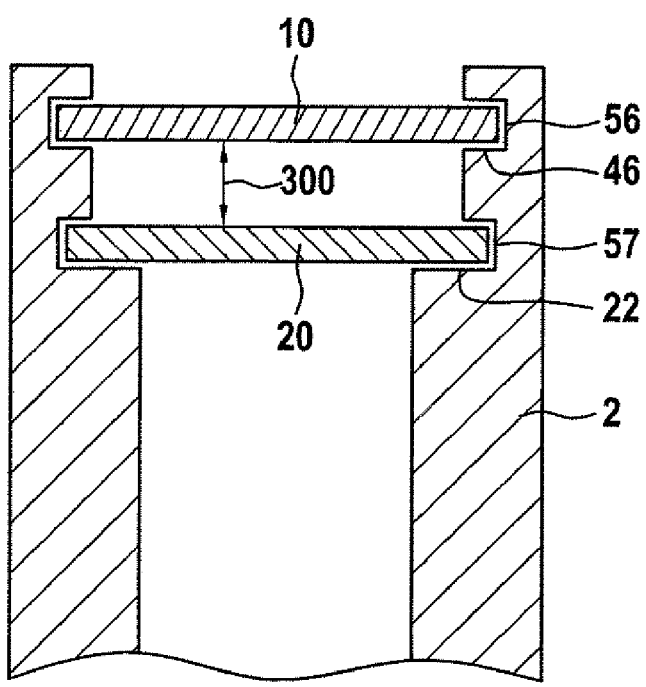
FIG. 18 is a cross sectional view showing another embodiment of an assembly comprising a gas inlet opening and a sensor housing.

FIG. 18 shows in a cross-sectional view another arrangement for assembling an outer housing 2 with a first, upper and a second, lower slotted disks 10, 20. The design of the outer housing 2 corresponds to the design according to FIG. 14. The outer housing 2 is provided with a second groove 22 and a first groove 46 on the top side on the circumference. Projections 52 (FIG. 11) in the outer housing 2 and corresponding recesses 51 (FIG. 11) in the slotted disks 10, 20 for radially positioning the slotted disks 10, 20 and securing them against rotation are not shown in this cross-sectional view in FIG. 18. In addition to the grooves 22, 46, a first, horizontal notch 56 is prepared on the first groove 46 and a second, horizontal notch 57 is prepared on the second groove 22. These notches 56, 57 lockingly receive the first and second slotted disks 10, 20. The first and second slotted disks 10, 20 have a diameter that is minimally greater than the internal size of the grooves 46, 22, so that the first and second slotted disks 10, 20 are always placed in the notches 56, 57 on the outer circumference and horizontal separation of the first and second slotted disks 10, 20 from this position is prevented from occurring. In addition, the first and second slotted disks 10, 20 can be secured against motion and rotation at the grooves 22, 46 and notches 56, 57, preferably with a bonded connection.

While specific embodiments of the invention have been described in detail to illustrate the application of the principles of the invention, it will be understood that the invention may be embodied otherwise without departing from such principles.

What is claimed is:

1. An infrared optical gas-measuring device comprising:
    a gas inlet opening for a gas sample to be analyzed in an infrared optical gas sensor, the gas inlet opening comprising two slotted or perforated disks, each of said disks defining transparent and gas-permeable elements and nontransparent and gas-impermeable elements;
    an outer housing;
    at least one infrared radiation source, said slotted disks or perforated disks comprising a surface reflective in the infrared optical range on the underside of each of said nontransparent and gas-impermeable elements and said slotted or perforated disks being arranged one on top of another at a distance such that the transparent and gas-permeable elements of one of said two slotted disk or perforated disks are covered in a vertical axial direction by the nontransparent and gas-impermeable elements of another of said two slotted or perforated disks, wherein said surface reflective in the infrared optical range of each of said nontransparent and gas-impermeable elements of an upper of said slotted disks or perforated disks reflects infrared radiation of said infrared radiation source, that has passed through said each of said transparent and gas-permeable elements of a lower of said slotted disks or perforated disks back through said transparent and gas-permeable elements of said lower of said slotted disks or perforated disks.

2. An optical gas-measuring device in accordance with claim 1, wherein the transparent and gas-permeable elements and the nontransparent and gas-impermeable elements are slotted circle segments arranged in the slotted disks as transparent and gas-permeable elements alternating with full circle segments as nontransparent and gas-impermeable elements concentrically in relation to a reference point.

3. An optical gas-measuring device in accordance with claim 1, wherein the transparent and gas-permeable elements of the slotted disks comprise slotted ring segments arranged concentrically in relation to a reference point.

4. An optical gas-measuring device in accordance with claim 1, wherein the transparent and gas-permeable elements of the slotted disks comprise slotted segments, which originate from a reference point and are arranged in a radiate pattern.

5. An optical gas-measuring device in accordance with claim 1, wherein the outer housing has a bottom section with an arrangement of light passages and at least one functional module and a horizontal position of a reference point on the slotted disk or on the perforated disk, to establish the covering in the vertical axial direction, is selected corresponding to the arrangement of light passages in the bottom section as well as to a position of the at least first infrared radiation source and to a position of at least one optical infrared detector in the at least one functional module under the bottom section.

6. An optical gas-measuring device in accordance with claim 1, wherein at least one groove, which receives the slotted disks or perforated disks, is arranged in the outer housing.

7. An optical gas-measuring device in accordance with claim 1, wherein the slotted disks or perforated disks are held by least one folded-back part at a predetermined distance from one another.

8. An optical gas-measuring device in accordance with claim 1, wherein the gas inlet opening further comprises at least one spacer element and the slotted disks or perforated disks are held by the at least one spacer element at a predetermined distance from one another.

9. An optical gas-measuring device in accordance with claim 8, wherein the spacer element and the slotted disks or perforated disks together form a gas inlet element or a gas inlet module.

10. An optical gas-measuring device in accordance with claim 1, wherein a recess in the slotted disks or in the perforated disks and a corresponding projection in the outer housing is provided as a radial positioning and/or means securing the slotted disks or perforated disks against rotation in relation to one another and to the outer housing.

11. An optical gas-measuring device in accordance with claim 1, wherein the gas inlet opening further comprises a spacer element, which maintains the first and second slotted disk or perforated disk at a center or reference point at a predetermined distance from each other.

12. An optical gas-measuring device in accordance with claim 1, further comprising:
    a bottom section with light passages designed as transparent disks, said bottom section being positioned within said outer housing and cooperating with said outer housing to define a measuring gas cell within said outer housing between said bottom section and said two slotted or perforated disks; and
    one or more electronic components and one or more infrared detectors positioned within said outer housing on a side of said bottom section opposite to said measuring gas cell, said bottom section separating said electronic components and infrared detectors gas-tightly from said measuring gas cell by means of a bonded connection.

13. An optical gas-measuring device in accordance with claim 1, further comprising:
    a functional module defining a functional module space with a wall dividing the functional module space into a first functional area and a second functional area separated from each other gas-tightly by means of the wall and/or electrically insulated from each other.

14. An optical gas-measuring device in accordance with claim 1, wherein:
    the slotted disks or perforated disks have an outer shape;
    the outer housing gas has an outer shape; and
    the outer shape of the slotted disks or perforated disks and the outer shape of the outer housing are coordinated with one another and the outer housing holdingly receives the slotted disks or perforated disks.

15. An optical gas-measuring device in accordance with claim 1, wherein the outer housing comprises a plastic material, which is provided, on an interior surface with a coating reflective in the infrared optical range on an inside.

16. An optical gas-measuring device in accordance with claim 1, wherein the outer housing is pot-shaped and the pot-shaped form of the outer housing is cylindrically round, oval or elliptical, cubic, rectangular, square or polygonal.

17. A method of infrared optical gas-measurement, the method comprising the steps of:
    providing a gas inlet opening for a gas sample to be analyzed, the gas inlet opening comprising two slotted or perforated disks, each of said disks defining transparent and gas-permeable elements and nontransparent and gas-impermeable elements, said slotted disks or perforated disks comprising a surface reflective in the infrared optical range on the underside of each of said nontransparent and gas-impermeable elements;
    providing an outer housing;
    providing an infrared radiation source;

arranging the slotted or perforated disks one on top of another at a distance such that the transparent and gas-permeable elements of one of the two slotted or perforated disks are covered in a vertical axial direction by the nontransparent and gas-impermeable elements of another of the two slotted or perforated disks to provide an infrared optical gas sensor; and analyzing the gas sample with the infrared optical gas sensor, wherein said surface reflective in the infrared optical range of each of said nontransparent and gas-impermeable elements of an upper of said slotted disks or perforated disks reflects infrared radiation of said infrared radiation source, that has passed through said each of said transparent and gas-permeable elements of a lower of said slotted disks or perforated disks back through said transparent and gas-permeable elements of said lower of said slotted disks or perforated disks.

18. An infrared optical gas-measuring device comprising:

an outer housing with an opening;

infrared radiation source;

an outer disk with transparent slotted circle segments comprising transparent and gas-permeable elements alternating with nontransparent slotted circle segments comprising nontransparent and gas-impermeable elements with a surface reflective in the infrared optical range on a housing interior side of said nontransparent slotted circle segments of said outer disk; and an inner disk with transparent slotted circle segments comprising transparent and gas-permeable elements alternating with nontransparent slotted circle segments comprising nontransparent and gas-impermeable elements with a surface reflective in the infrared optical range on the housing interior side of said nontransparent slotted circle segments of said inner disk, said outer disk being connected to said housing and said inner disk being connected to said housing on the housing interior side of said outer disk and spaced inwardly from said outer slot disk with respect to an axial direction of said outer housing, said transparent slotted circle segments of said outer disk being axially aligned with said nontransparent slotted circle segments of said inner disk and said nontransparent slotted circle segments of said outer disk being axially aligned with said transparent slotted circle segments of said inner disk, wherein said surface reflective in the infrared optical range of each of said nontransparent slotted circle segments of said outer disk reflects infrared radiation of said infrared radiation source, that has passed through said transparent slotted circle segments of said inner disk, back through said transparent slotted circle segments of said inner disk.

19. An optical gas-measuring device in accordance with claim 18, wherein:

said outer disk has a positioning structure at an outer peripheral edge;

said inner disk has a positioning structure at an outer peripheral edge;

said outer housing has a radial positioning structures engaging said positioning structure of said outer disk and said inner disk to act against rotation in relation to one another and in relation to the outer housing.

20. An optical gas-measuring device in accordance with claim 19, wherein:

said outer disk comprises a plastic material with said surface of said outer disk provided as a coating reflective in the infrared optical range on an inside;

said inner disk comprises a plastic material with said surface of said inner disk provided as a coating reflective in the infrared optical range on an inside; and said outer housing comprises a plastic material, which is provided on an interior surface with a coating reflective in the infrared optical range on an inside.

* * * * *